US011839501B2

(12) United States Patent
Takahashi et al.

(10) Patent No.: US 11,839,501 B2
(45) Date of Patent: Dec. 12, 2023

(54) IMAGE CREATION DEVICE

(71) Applicant: Shimadzu Corporation, Kyoto (JP)

(72) Inventors: Wataru Takahashi, Kyoto (JP); Shota Oshikawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 825 days.

(21) Appl. No.: 16/959,814

(22) PCT Filed: Jan. 9, 2018

(86) PCT No.: PCT/JP2018/000154
§ 371 (c)(1),
(2) Date: Oct. 19, 2020

(87) PCT Pub. No.: WO2019/138438
PCT Pub. Date: Jul. 18, 2019

(65) Prior Publication Data
US 2021/0030374 A1 Feb. 4, 2021

(51) Int. Cl.
*G06K 9/00* (2022.01)
*G08B 17/12* (2006.01)
(Continued)

(52) U.S. Cl.
CPC .............. *A61B 6/03* (2013.01); *A61B 6/481* (2013.01); *A61B 6/487* (2013.01); *A61B 6/504* (2013.01);
(Continued)

(58) Field of Classification Search
CPC ....... A61B 6/03; A61B 2576/02; A61B 6/487; A61B 6/486; A61B 6/48; A61B 6/52;
(Continued)

(56) References Cited

U.S. PATENT DOCUMENTS

| 2005/0100208 | A1 | 5/2005 | Suzuki et al. |
| 2010/0086189 | A1* | 4/2010 | Wang ........................ G06T 5/00 |
| | | | 340/600 |
| 2016/0175614 | A1 | 6/2016 | Taguchi et al. |

FOREIGN PATENT DOCUMENTS

| JP | 2011-161104 A | 8/2011 |
| JP | 2012-245142 A | 12/2012 |

(Continued)

OTHER PUBLICATIONS

Written Opinion for PCT application No. PCT/JP2018/000154, dated Mar. 20, 2018, submitted with a machine translation.
(Continued)

*Primary Examiner* — Don K Wong
(74) *Attorney, Agent, or Firm* — Muir Patent Law, PLLC

(57) ABSTRACT

An image generating device for generating an image which is an X-ray image of an area including a bone portion of a subject with the bone portion removed has a control unit 70 including: a DRR imager 81 configured to generate a first DRR image of an area including a bone portion and a second DRR image showing the bone portion, by performing, for a set of CT image data of an area including the bone portion of a subject, a virtual fluoroscopic projection simulating a geometric fluoroscopy condition of an X-ray irradiator and an X-ray detector for the subject; a training section 82 configured to generate a machine learning model for recognizing the bone portion, by performing machine learning using the first DRR image and the second DRR image serving as a training image; an image converter 83 configured to perform conversion of the X-ray image of the area including the bone portion of the subject, using the machine learning model trained in the training section 82, to generate an image showing the bone portion; and a bone portion subtractor 84 configured to subtract the image showing the
(Continued)

bone portion from the X-ray image of the area including the bone portion of the subject.

7 Claims, 27 Drawing Sheets

(51) Int. Cl.
    *A61B 6/03* (2006.01)
    *A61B 6/00* (2006.01)
    *G06T 7/00* (2017.01)
(52) U.S. Cl.
    CPC ............ *A61B 6/505* (2013.01); *A61B 6/5211* (2013.01); *G06T 7/0012* (2013.01); *G06T 2207/10121* (2013.01); *G06T 2207/10124* (2013.01); *G06T 2207/20081* (2013.01); *G06T 2207/20084* (2013.01); *G06T 2207/30008* (2013.01); *G06T 2207/30101* (2013.01)
(58) Field of Classification Search
    CPC ... A61B 6/5288; A61B 6/5258; A61B 6/5211; A61B 6/5294; G06T 11/003; G06T 11/008; G06T 2207/10121; G06T 2207/10124; G06T 2207/20084
    See application file for complete search history.

(56) References Cited

FOREIGN PATENT DOCUMENTS

| JP | 2014-000287 A | 1/2014 |
| JP | 2015-226694 A | 12/2015 |
| JP | 2016-116659 A | 6/2016 |

OTHER PUBLICATIONS

First Office Action dated Feb. 25, 2023 for corresponding Chinese Patent Application No. 201880085992.9.
Notice of Allowance dated Aug. 25, 2023 issued for the corresponding Chinese Patent Application No. 201880085992.9.

* cited by examiner

X33

IMAGE CREATION DEVICE

TECHNICAL FIELD

The present invention relates to an image generating device configured to generate an image showing a specific region from an X-ray image, using digitally reconstructed radiography (DRR) images.

BACKGROUND ART

In an image processing technique called bone suppression (or by other names), which is performed for obtaining an X-ray image of a subject with the bone portions removed, dual energy subtraction imaging has conventionally been performed. Dual energy subtraction is a technique of removing bone portions from an X-ray image by taking images of a subject two times at different levels of tube voltage and performing weighted subtraction of the two X-ray images (see Patent Literature 1).

An imaging method called digital subtraction angiography (DSA) is used for taking angiographic images. A procedure of this imaging is as follows: An X-ray image of a subject with no contrast dye injected is initially generated as a mask image. An X-ray image of the same subject with a contrast dye injected into blood vessels is subsequently generated as a live image. An image processing operation for subtracting the mask image from the live image is performed to generate a subtraction image which shows the dye-injected blood vessels (see Patent Literature 2).

In the case of using X-ray photography to display a stent placed in the body of a subject, accumulating a number of images of the stent has been common practice to generate a clearer display of the stent image (see Patent Literature 3).

CITATION LIST

Patent Literature

Patent Literature 1: JP 2012-245142 A
Patent Literature 2: JP 2015-226694 A
Patent Literature 3: JP 2014-000287 A

SUMMARY OF INVENTION

Technical Problem

The bone suppression and angiographic imaging both include subtraction of two X-ray images. Therefore, an artifact occurs if there is a misalignment between the images due to a body motion of the subject from the point in time of the acquisition of the first image to that of the second image. Accordingly, it has been necessary to restrict body motions of the subject to prevent such an artifact, or perform various kinds of processing to reduce the artifact.

In the case of displaying an image of a stent, there is the problem that the image of the stent cannot be recognized by X-ray fluorography if a bioabsorbable stent is used.

The present invention has been developed to solve the previously described problems. Its objective is to provide an image generating device capable of generating an image showing a specific region from an X-ray image by machine learning using DRR images.

Solution to Problem

The invention according to claim 1 includes: a DRR imager configured to generate a first DRR image showing an area including a specific region of a subject and a second DRR image showing the specific region, by performing, for a set of CT image data of the area including the specific region of the subject, a virtual fluoroscopic projection simulating a geometric fluoroscopy condition of an X-ray irradiator and an X-ray detector for the subject; a training section configured to generate a machine learning model for recognizing the specific region, by performing machine learning using the first DRR image and the second DRR image serving as a training image; and an image converter configured to perform conversion of an X-ray image of the area including the specific region of the subject into an image showing the specific region, using the machine learning model that has undergone the training in the training section, to generate an image showing the specific region.

In the invention according to claim 2, which is a specific mode of the invention according to claim 1, the specific region is a bone portion, and the image generating device further includes a bone portion subtractor configured to subtract an image showing the bone portion from the X-ray image.

In the invention according to claim 3, which is a specific mode of the invention according to claim 1, the specific region is all regions except the bone portion of the subject.

In the invention according to claim 4, which is a specific mode of the invention according to claim 1, the specific region is a blood vessel with a contrast dye injected.

In the invention according to claim 5, which is a specific mode of the invention according to claim 4, the first DRR image is a DRR image obtained by removing the dye-injected blood vessel from a DRR image including the dye-injected blood vessel, while the X-ray image is an X-ray image with no contrast dye injected, and the image generating device further includes a blood vessel adder configured to add an image showing the dye-injected blood vessel to the X-ray image.

In the invention according to claim 6, which is a specific mode of the invention according to claim 1, the specific region is a stent placed in the body of the subject, and the image generating device further includes a stent adder configured to add an image showing the stent to the X-ray image.

Advantageous Effects of Invention

The invention according to claim 1 enables the generation of an image showing a specific region from a single X-ray image by machine learning using DRR images.

By the invention according to claim 2, in the case of obtaining an image which is an X-ray image of a subject with a bone portion removed, an image of the bone portion is extracted from a single X-ray image, and the extracted image is subtracted from the X-ray image, whereby an image which is an X-ray image of the subject with the bone portion removed can be easily obtained. This prevents an artifact due to a body motion of the subject as well as halves the necessary amount of exposure dose for the imaging.

By the invention according to claim 3, in the case of obtaining an image which is an X-ray image of a subject with a bone portion removed, all regions except the bone portion of the subject are extracted from a single X-ray image, whereby an image which is an X-ray image of the subject with the bone portion removed can be easily obtained. This prevents an artifact due to a body motion of the subject as well as halves the necessary amount of exposure dose for the imaging.

By the invention according to claim 4 or 5, in the case of generating an image of a blood vessel of a subject with a contrast dye injected, an image of the dye-injected blood vessel is extracted from a single X-ray image, whereby an image of the blood vessel can be obtained. This prevents an artifact due to a body motion of the subject as well as halves the necessary amount of exposure dose for the imaging.

By the invention according to claim 6, in the case of generating an image by adding a stent placed in the body of the subject to an X-ray image of a subject, even when the stent cannot be recognized on the X-ray image, the location of the stent can be identified based on feature quantities around the stent, and an image representing the stent can be added to and displayed on the X-ray image.

DESCRIPTION OF EMBODIMENTS

Figure 1:
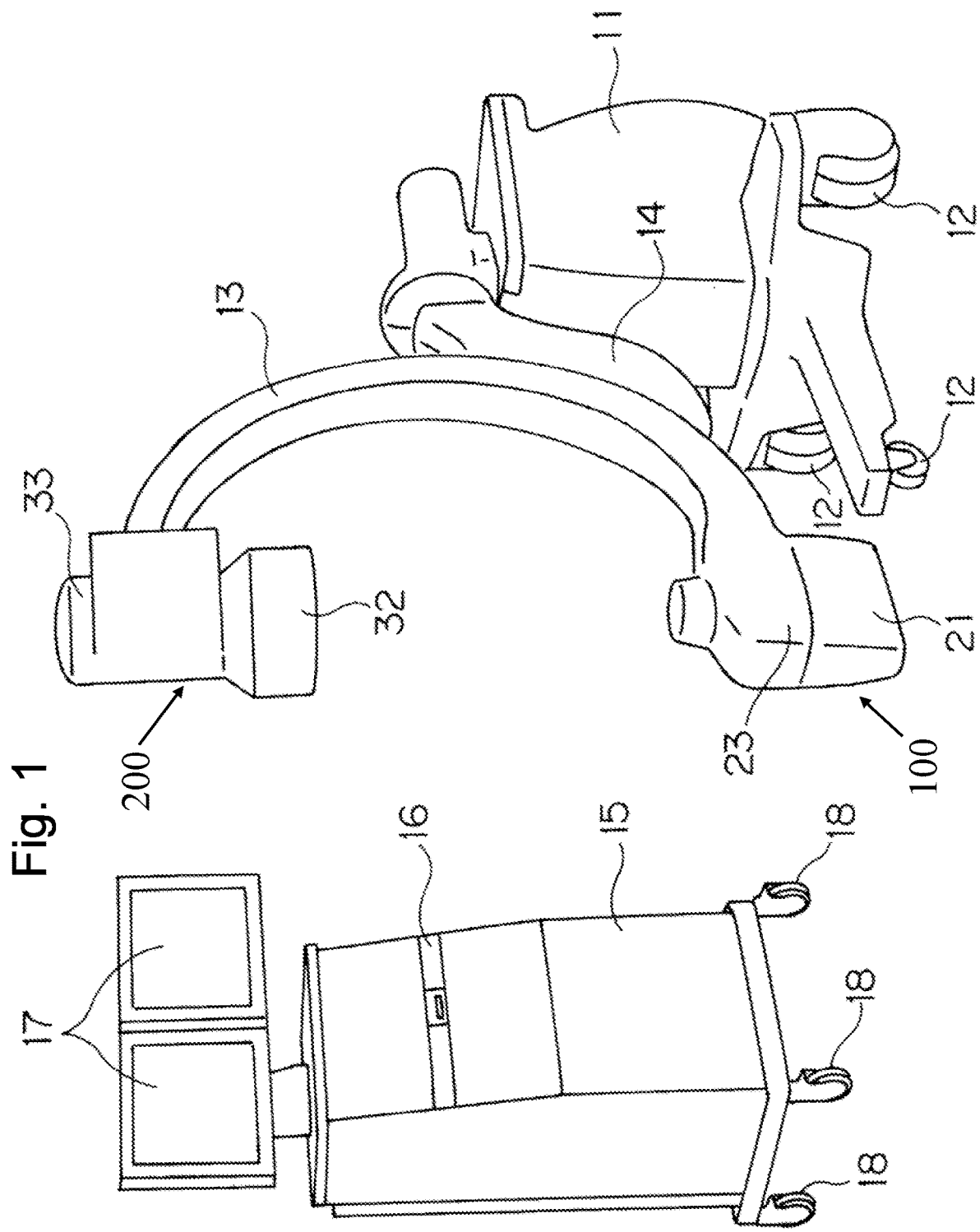
FIG. 1 is a perspective view of an X-ray fluorography device to be connected to an image generating device according to the present invention and be used for performing X-ray fluorography.

Modes for carrying out the present invention are hereinafter described based on the drawings. FIG. 1 is a perspective view of an X-ray fluorography device to be connected to an image generating device according to the present invention and be used for performing X-ray fluorography.

This X-ray fluorography device is configured to perform X-ray fluoroscopy and X-ray photography. The device has a device body 11 which can be rolled by wheels 12. The X-ray fluorography device includes an X-ray irradiator 100 and an X-ray detector 200 as well as a C-arm 13 supporting the X-ray irradiator 100 and X-ray detector 200. The X-ray irradiator 100 includes an X-ray tube 21 and a collimator 23 configured to form an X-ray irradiation field by restricting the irradiation area of the X-rays emitted from the X-ray tube 21. The X-ray detector 200 includes an image intensifier (I. I.) 32 configured to detect X-rays emitted from the X-ray tube 21 and passing through a patient as the subject and to generate a visual image from the X-rays, as well as a camera 33 configured to take a photograph of the visual image generated by the image intensifier 32.

The C-arm 13 is shaped like an arc and configured to support the X-ray irradiator 100 and X-ray detector 200. This C-arm 13 is supported in a slidable manner in relation to an arm support 14. The arm support 14 is supported in a movable manner in both horizontal and vertical directions in relation to the device body 11. The transfer of the C-arm 13 is carried out by an operator holding a handle (not shown) and changing the position of the C-arm 13.

The X-ray fluorography device is equipped with a monitor unit 15 including a display section 17, such as an LCD for displaying X-ray images based on the X-rays detected by the X-ray detector 200, as well as an input section 16 including a retractable keyboard and other components. The monitor unit 15 can be rolled by the action of wheels 18.

Figure 2:
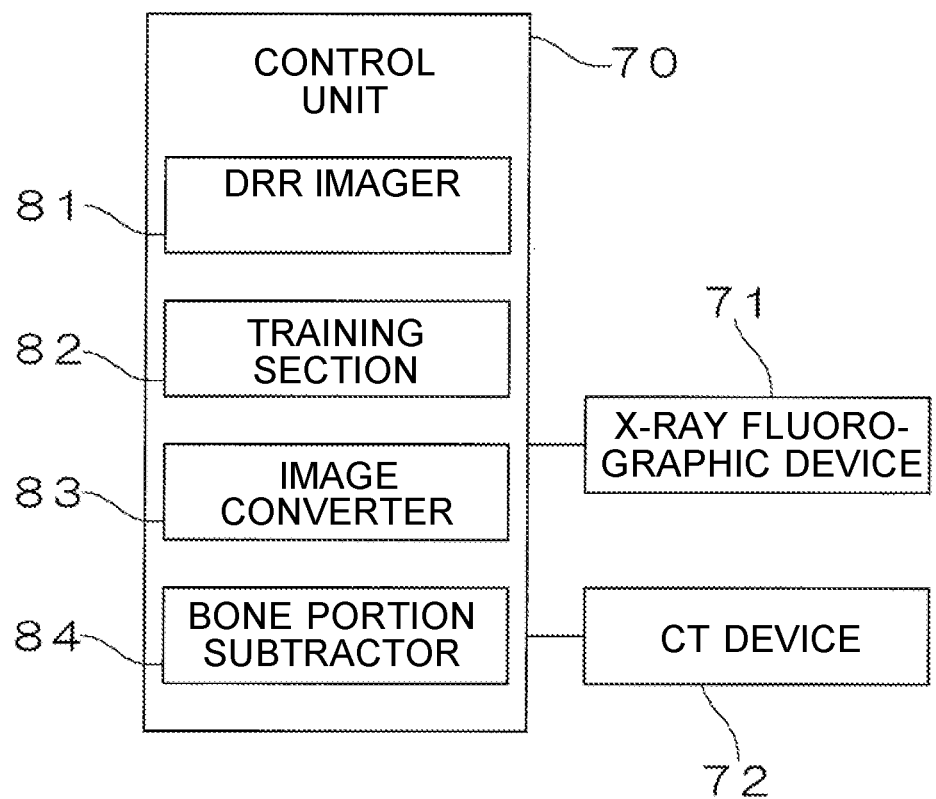
FIG. 2 is a block diagram showing the control system of an image generating device according to the first embodiment of the present invention.

The configuration of the image generating device according to the first embodiment of the present invention is hereinafter described. FIG. 2 is a block diagram showing the control system of the image generating device according to the first embodiment of the present invention.

The image generating device according to the first embodiment is configured to generate an image which is an X-ray image of an area including the bone portions of a subject with the bone portions removed. The device includes a control unit 70 configured to control the entire device, including a CPU as a processor for performing logic operations, a ROM in which necessary operation programs for the device control are stored, a RAM to be used for temporarily storing data and other pieces of information during the control process, as well as other related elements. The control unit 70 is connected to the X-ray fluorography device 71 shown in FIG. 1. The control unit 70 is also connected online or offline to a computed tomography (CT) device 72, which performs CT scan for a subject and stores the CT images.

As will be described later, the control unit 70 includes: a DRR imager 81 configured to generate a first DRR image of an area including a bone portion and a second DRR image showing the bone portion, by performing, for a set of CT image data of an area including the bone portion of a subject, a virtual fluoroscopic projection simulating a geometric fluoroscopy condition of an X-ray irradiator 100 and an X-ray detector 200 for the subject; a training section 82 configured to generate a machine learning model for recognizing the bone portion, by performing machine learning using the first DRR image and the second DRR image serving as a training image; an image converter 83 configured to perform conversion of the X-ray image of the area including the bone portion of the subject, using the machine learning model that has undergone the training in the training section 82, to generate an image showing the bone portion; and a bone portion subtractor 84 configured to subtract the image showing the bone portion from the X-ray image of the area including the bone portion of the subject.

An operation using the image generating device having the previously described configuration for detecting the region of a bone portion of a subject and generating an image which is an X-ray image of an area including the bone portion of the subject, with the bone portion removed, is hereinafter described.

Figure 3:
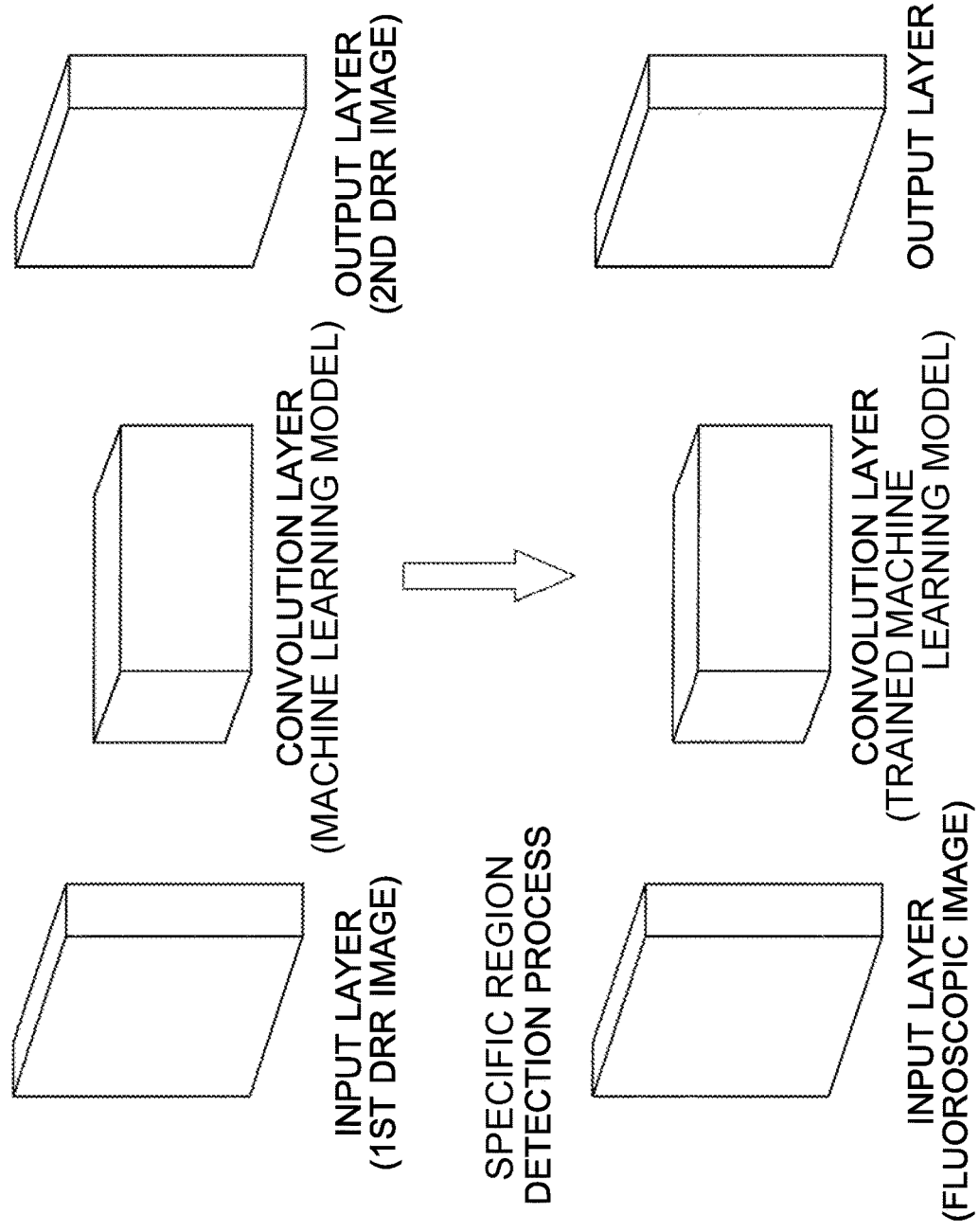
FIG. 3 is a model diagram for explaining the process of detecting a specific region of a subject using machine learning by an image generating device according to the present invention.

The basic idea for identifying the location of a bone portion is initially described. FIG. 3 is a model diagram for explaining the process of detecting a specific region of a subject using machine learning by an image generating device according to the present invention.

In order to identify the location of a bone portion by using machine learning, a machine learning model should initially be trained. In the process of training the machine learning model, a convolution layer to be used as the machine learning model is trained by machine learning, using first DRR images including the area of a specific region as the input layer and second DRR images showing the specific portion as the output layer. Subsequently, the region of the bone portion should be detected. In the process of detecting the region of the bone portion, an X-ray fluoroscopic image is used as the input layer and converted through the trained machine learning model to obtain an image showing the region of the bone portion as the output layer.

Figure 4:
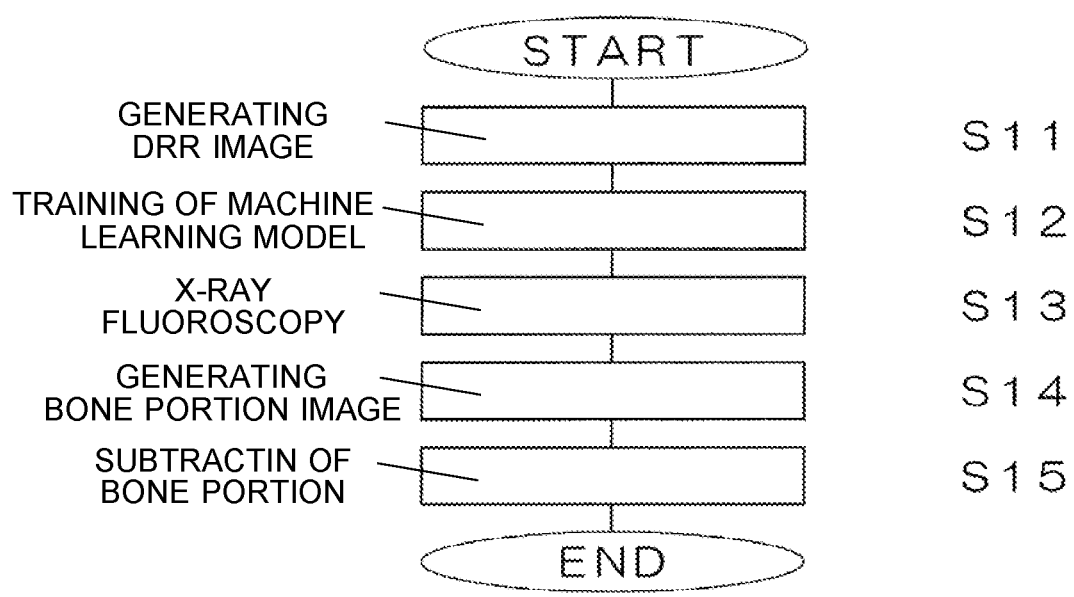
FIG. 4 is a flowchart showing an operation performed by an image generating device according to the present invention when generating an image which is an X-ray image of an area including the bone portions of a subject with the bone portions removed.

The operation of detecting the location of a specific region by the previously described processes is hereinafter described in detail. FIG. 4 is a flowchart showing an operation performed by an image generating device according to the present invention when generating an image which is an X-ray image of an area including the bone portions of a subject with the bone portions removed.

When the image generating operation is to be performed, the DRR imager 81 shown in FIG. 2 generates a first DRR image showing an area including bone portions and a second DRR image showing the bone portions in advance of the execution of X-ray fluoroscopy for a subject, by performing, for a set of four-dimensional CT image data obtained from the CT device 72, a virtual fluoroscopic projection simulating a geometric fluoroscopy condition of the X-ray irradiator 100 and X-ray detector 200 of the X-ray fluorography device shown in FIG. 1 (Step S11). When the second DRR image showing the bone portions is to be generated, each area with the CT values exceeding a specific level is selected as a region of the bone portions for the generation of the DRR image. For example, each area with the CT value equal to or greater than 200 HU (Hounsfield Unit) may be recognized as a region of the bone portions for the generation of the DRR image. The "four-dimensional CT image data" is a set of data of the three-dimensional CT images of an area including the bone portions consecutively taken with the passage of time in a plurality of consecutive phases of respiration. Three-dimensional CT image data may also be used in place of the four-dimensional CT image data.

Figure 5:
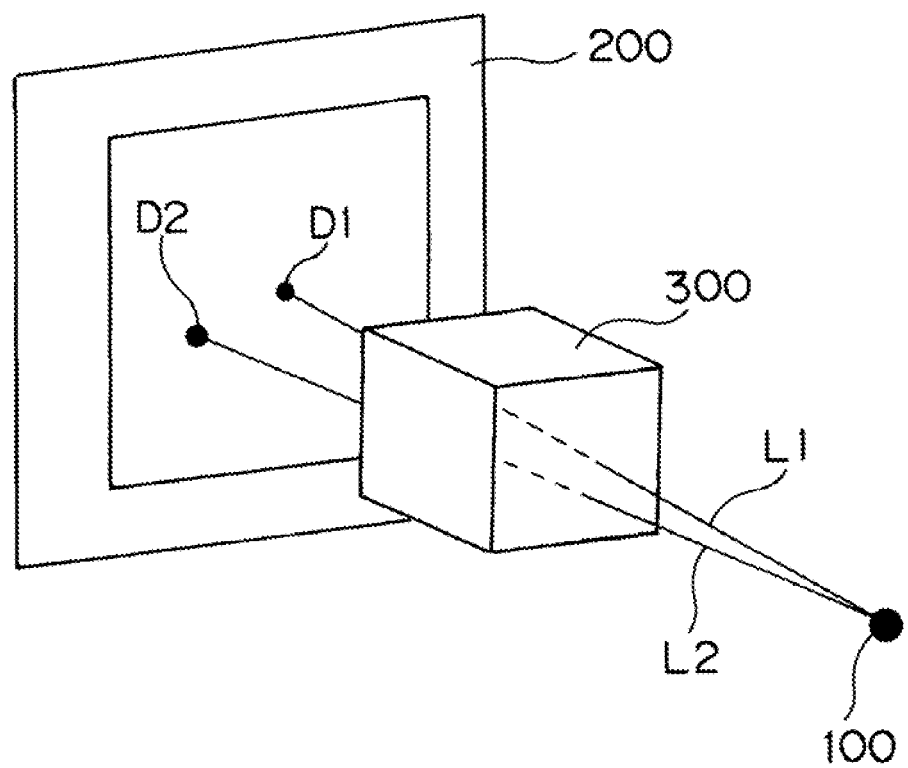
FIG. 5 is a diagram schematically illustrating the situation in which a DRR image is generated by virtual fluoroscopy which simulates a geometric fluoroscopy condition of an X-ray irradiator 100 and an X-ray detector 200 of an X-ray fluorography device.

FIG. 5 is a diagram schematically illustrating the situation in which a DRR image is generated by virtual fluorography which simulates a geometric fluoroscopy condition of an X-ray irradiator 100 and an X-ray detector 200 of an X-ray fluorography device.

In FIG. 5, reference sign 300 denotes CT image data. The CT image data 300 is a set of three-dimensional voxel data which is a collection of a plurality of sets of two-dimensional CT image data. For example, the CT image data 300 has a structure in which approximately 200 pieces of two-dimensional images of 512×512 pixels are layered in a direction crossing the body of a subject (along the line segment L1 or L2 shown in FIG. 5).

When a DRR image is to be generated by the DRR imager 81, a virtual fluoroscopic projection is performed on the CT image data 300 as follows: The three-dimensional CT image data 300 is placed within a virtual space on a computer, and the geometry, which is a geometric arrangement of an X-ray photography system, is reproduced within the same virtual space on the computer. In the present embodiment, the X-ray irradiator 100 and X-ray detector 200 are respectively arranged on opposite sides of the CT image data 300. The arrangement of the CT image data 300, X-ray irradiator 100 and X-ray detector 200 has the same geometry as that of the subject, X-ray irradiator 100 (including the X-ray tube 21 and collimator 23) and X-ray detector 200 (including the image intensifier 32 and camera 33) arranged for the X-ray fluoroscopy with the X-ray fluorography device shown in FIG. 1. The "geometry" in the present context means the relationship of the geometric arrangement of the photographic target, X-ray irradiator 100 and X-ray detector 200.

In this situation, a large number of line segments L are set, with each line segment connecting the X-ray irradiator 100 and one of the pixels of the X-ray detector 200 through one of the pixels of the CT image data 300. For convenience of explanation, two line segments L1 and L2 are drawn in FIG. 5. On each line segment L, multiple calculation points are set, and the CT value at each calculation point is computed. For the computation of the CT value, interpolation is performed using the CT values in the CT data voxels surrounding the calculation point. Subsequently, the CT values at the calculation points on the line segment L are accumulated.

The accumulated value is converted into a line integral of the linear attenuation coefficient to calculate the amount of attenuation of the X-ray. Thus, a DRR image is generated.

In the process of generating a DRR image, one or more parameters for the generation of the DRR image, including one or both of the coordinates and angle of projection for the CT image data 300, are varied to generate the DRR image. Alternatively, an image processing operation including at least one of the operations of translation, rotation, deformation and resizing by a small amount is performed. The aim of the translation, rotation, deformation and resizing is to make it possible to more assuredly follow the specific region even when the position of the X-ray irradiator 100 and X-ray detector 200 is changed while the X-ray fluoroscopy is being performed.

The frame rate of the CT image data 300 from which the DRR image is generated is lower than that of the X-ray fluoroscopic image. However, it is possible to simulate the bone portion at a point in time between the frames in the DRR image by varying the parameters for the generation of the DRR image. This enables more accurate detection of the region of the bone portion.

The generated DRR image is further subjected to at least one of the operations of contrast change, noise addition and edge enhancement. The aim of the contrast change, noise addition and edge enhancement is to absorb differences in image quality between the DRR and X-ray images so that the region of the bone portion can be more assuredly recognized.

The previously described operations of varying the parameters for the generation of the DRR image, such as the coordinates and angle of projection, as well as the contrast change, noise addition and edge enhancement are randomly performed within a predetermined range, or alternatively, in such a manner as to give various changes at regular intervals. This produces a considerable number of DRR images from the CT image data 300 of a single subject. The considerable number of DRR images can be used to perform the training of a tailored machine learning model for each individual patient. It is also possible to generate a machine learning model using DRR images obtained for many patients.

In both the generation of the first DRR image and that of the second DRR image, the parameters including the coordinates and angle of projection in the geometric fluoroscopy condition should be varied under the same conditions, or the image processing including the rotation, deformation and resizing of the image should be performed under the same conditions.

Figure 6:
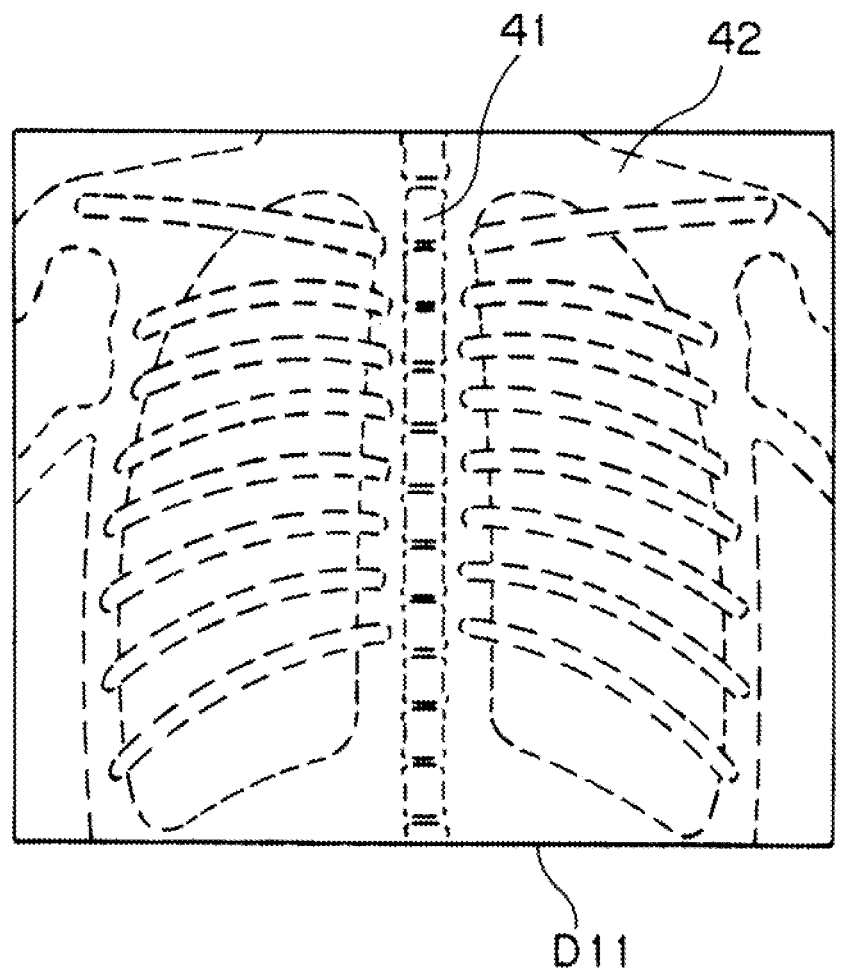
FIG. 6 is a rough sketch of the first DRR image D11 showing an area including bone portions 41 and soft tissues 42.
Figure 7:
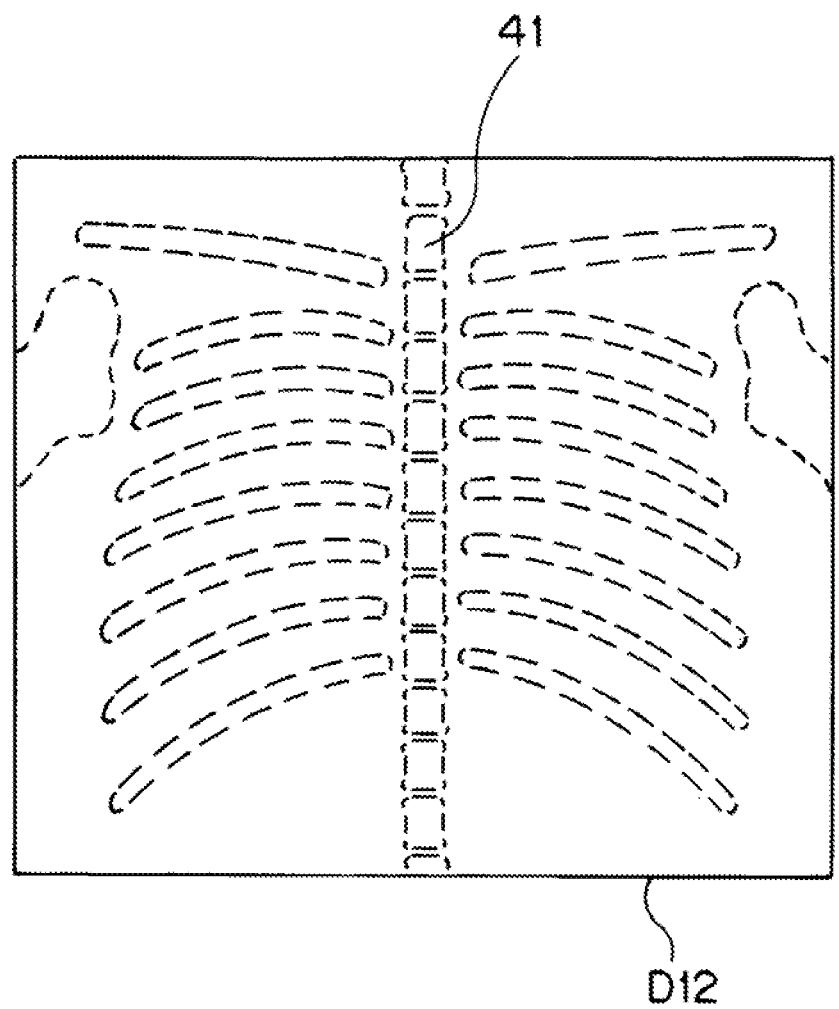
FIG. 7 is a rough sketch of the second DRR image D12 showing the bone portions 41.

FIG. 6 is a rough sketch of the first DRR image D11 showing an area including bone portions 41 and soft tissues 42 generated in the previously described manner. FIG. 7 is a rough sketch of the second DRR image D12 showing the bone portions 41. As described earlier, the second DRR image D12 is generated by accumulating the areas with CT values equal to or greater than 200 HU.

After the previously described processes have been completed, the training section 82 trains a machine learning model for recognizing the bone portions 41, by performing machine learning using the first DRR images D11 as the input layer and the second DRR images D12 as the output layer (Step S12). For example, fully convolutional networks (FCNs) are used in this machine learning. The convolutional neural networks used in the FCNs have a configuration as already shown in FIG. 3. That is to say, in the case of training the machine learning model, the input layer is the first DRR image D11, and the output layer is the second DRR image D12.

Figure 8:
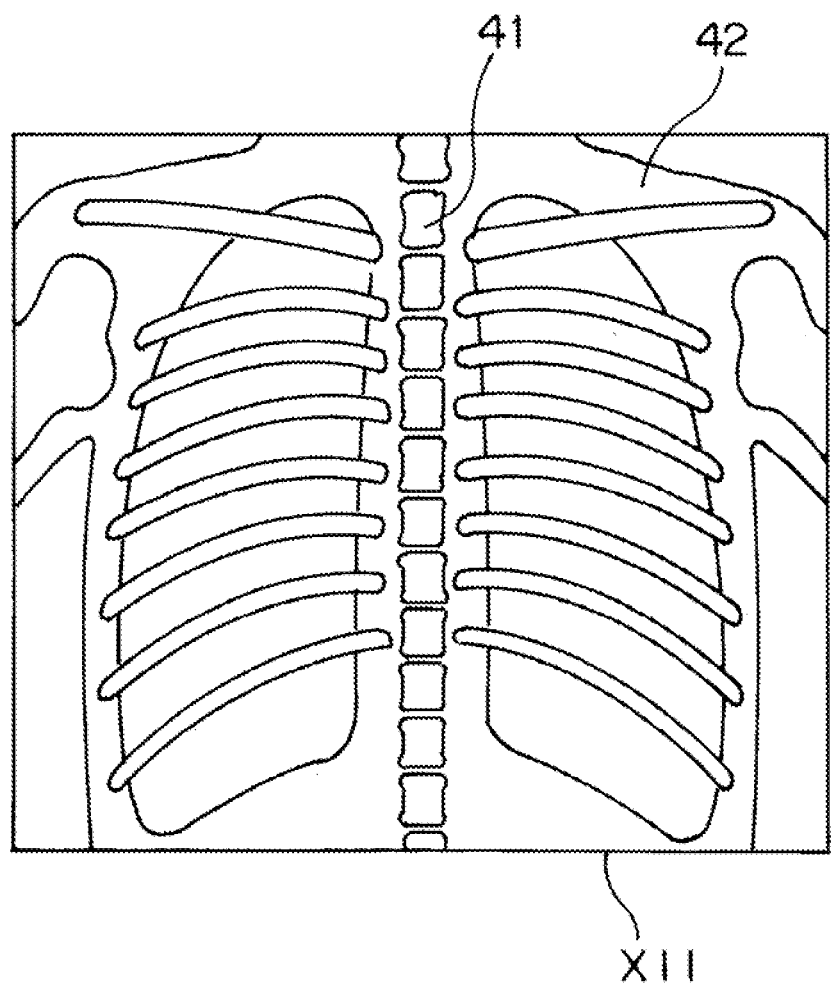
FIG. 8 is a rough sketch of an X-ray image X11 obtained by X-ray fluoroscopy.

After the machine learning model has been trained through the previously described processes, the X-ray fluoroscopy for the subject is initiated (Step S13). FIG. 8 is a rough sketch of an X-ray image X11 obtained by the X-ray fluoroscopy. The bone portions 41 and soft tissues 42 are shown on this X-ray image X11. X-ray fluoroscopy yields a plurality of X-ray images at a predetermined frame rate. FIG. 8 shows an X-ray image obtained in one of those frames. The same applies in the following descriptions.

Figure 9:
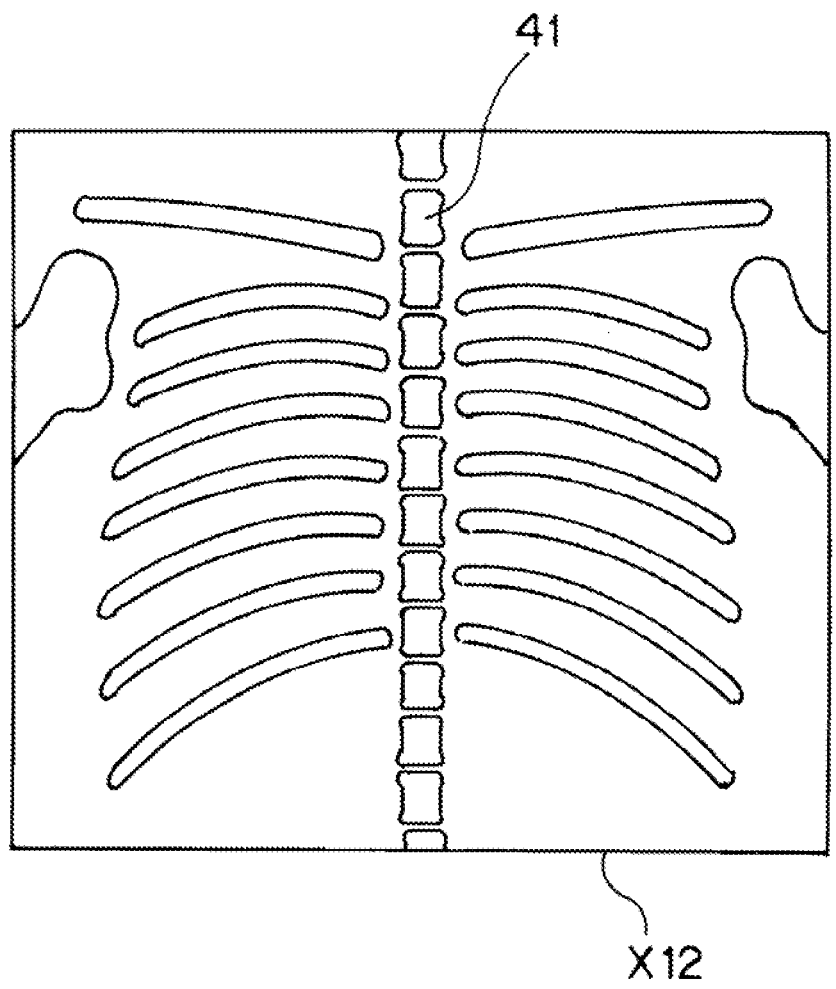
FIG. 9 is a rough sketch of an X-ray image X12 of the bone portions 41 obtained by conversion.

Next, the image converter 83 performs conversion using the machine learning model (convolution layer) that has undergone the training, to generate an image of the bone portions 41 (Step S14). Specifically, for the X-ray images obtained at a predetermined frame rate by the X-ray fluoroscopy, an X-ray image showing the bone portions 41 is generated as the output layer for each frame of the X-ray image, using the trained machine learning model. FIG. 9 is a rough sketch of an X-ray image X12 of the bone portions 41 obtained by the conversion.

Figure 10:
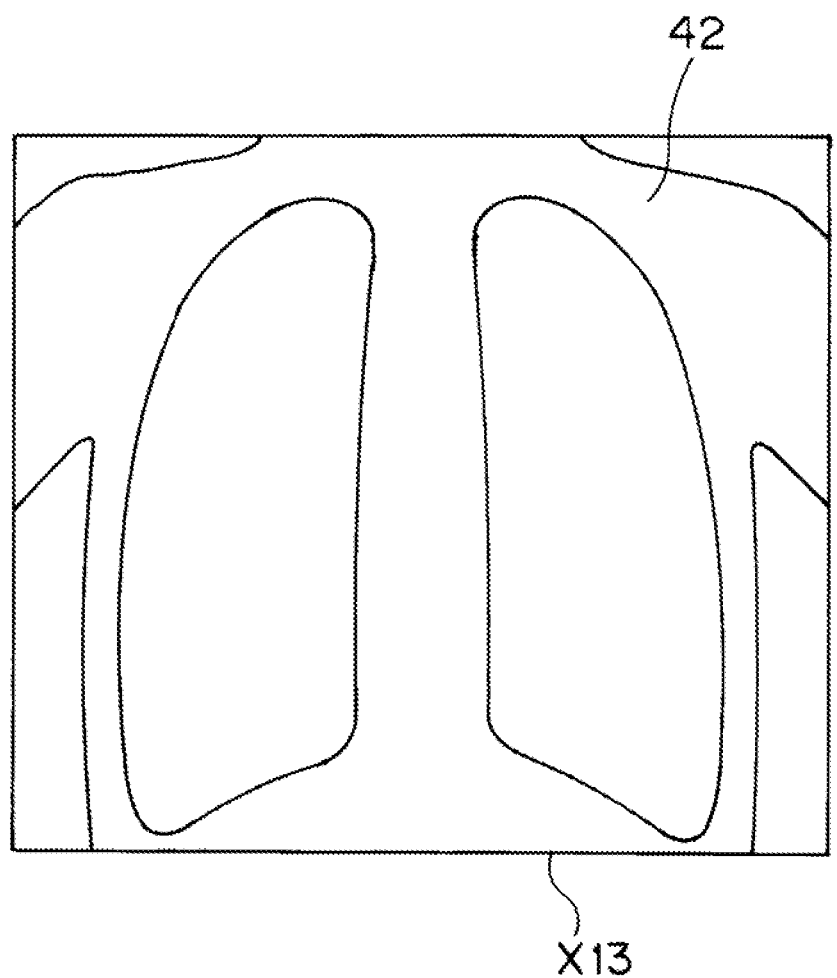
FIG. 10 is a rough sketch of an image X13 which is the X-ray image X11 of the subject with the bone portions removed.

Subsequently, the bone portion subtractor 84 subtracts the X-ray image X12 of the bone portions 41 obtained by the conversion, from the X-ray image X11 of the subject (Step S15). The resulting image is the X-ray image of the area including the bone portions of the subject, with the bone portions now removed. FIG. 10 is a rough sketch of an image X13 which is the X-ray image X11 of the subject with the bone portions 41 removed.

As described to this point, in the image generating device according to the present invention, the convolution layer to be used as the machine learning model is trained by machine learning using the first DRR images D11 as the input layer and the second DRR images D12 as the output layer. Subsequently, an X-ray image X11 as the input layer is converted by means of the trained machine learning model to obtain an X-ray image X12 showing the bone portions 41 as the output layer. Thus, an image showing the bone portions 41 can be obtained in real time. The X-ray image X12 showing the bone portions is subtracted from the X-ray image X11 to ultimately obtain an image X13 with the bone portions removed.

In the previously described embodiment, the X-ray fluoroscopic image may be blurred by a Gaussian filter (or the like) before being inputted into the machine learning model. In normal cases, DRR images are generated from low-resolution CT images, and therefore, are lower in resolution than X-ray fluoroscopic images. By blurring the X-ray fluoroscopic images to make them as low in resolution as the DRR images used in the training phase while reducing the noise level of the X-ray fluoroscopic images, the specific region can be more assuredly identified. Additionally, in the previously described embodiment, the DRR images and X-ray fluoroscopic images to be inputted into the machine learning model may be subjected to contrast normalization before being inputted. A local contrast normalization layer and local response localization layer may also be added to the hidden layers. All these modifications are similarly applicable in the following embodiments.

Figure 11:
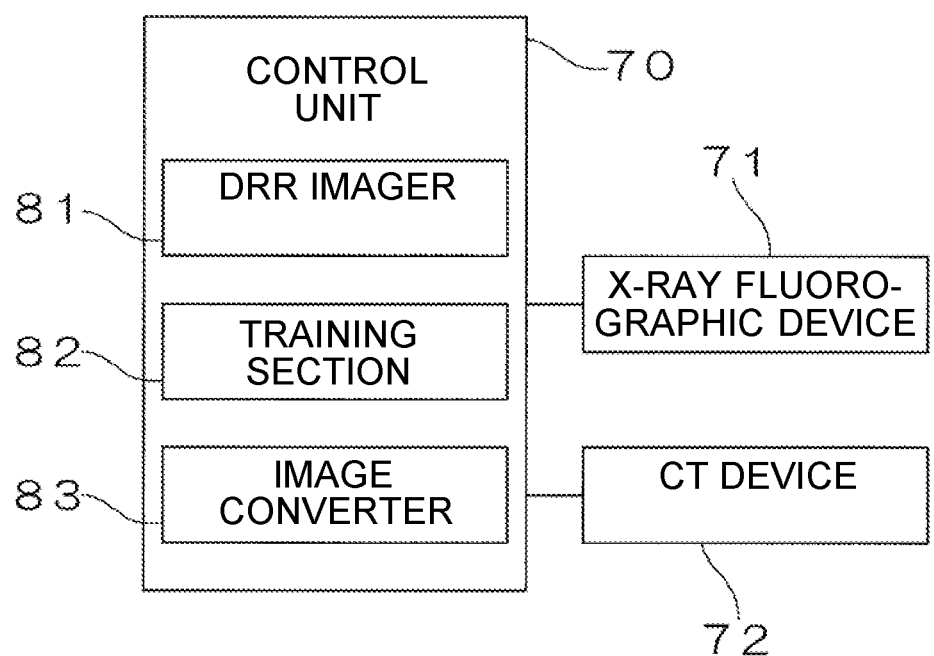
FIG. 11 is a block diagram showing the control system of an image generating device according to a modified example of the first embodiment of the present invention.

In the previously described embodiment, bone portions are selected as the specific region of the subject. It is also possible to conversely select all regions except the bone portions as the specific region of the subject. The following description deals with this type of modification. FIG. 11 is a block diagram showing the control system of an image generating device according to a modified example of the first embodiment of the present invention. Members similar to those used in the control system shown in FIG. 2 are denoted by the same reference signs. Detailed descriptions of those members will be omitted.

The DRR imager 81 in the control unit 70 of the image generating device according to this modified example of the first embodiment generates a first DRR image of an area including bone portions and a second DRR image showing all regions except the bone portions (soft tissues), by performing, for a set of CT image data of an area including the bone portions of the subject, a virtual fluoroscopic projection simulating a geometric fluoroscopy condition of the X-ray irradiator 100 and X-ray detector 200 for the subject. The training section 82 trains a machine learning model for recognizing the regions except the bone portions, by performing machine learning using the first DRR image and the second DRR image serving as a training image. The image converter 83 performs conversion of the X-ray image of the area including the bone portions of the subject, using the machine learning model trained in the training section 82, to generate an image showing the regions except the bone portions. The control unit 70 in this modified example does not have the bone portion subtractor 84 shown in FIG. 2.

Figure 12:
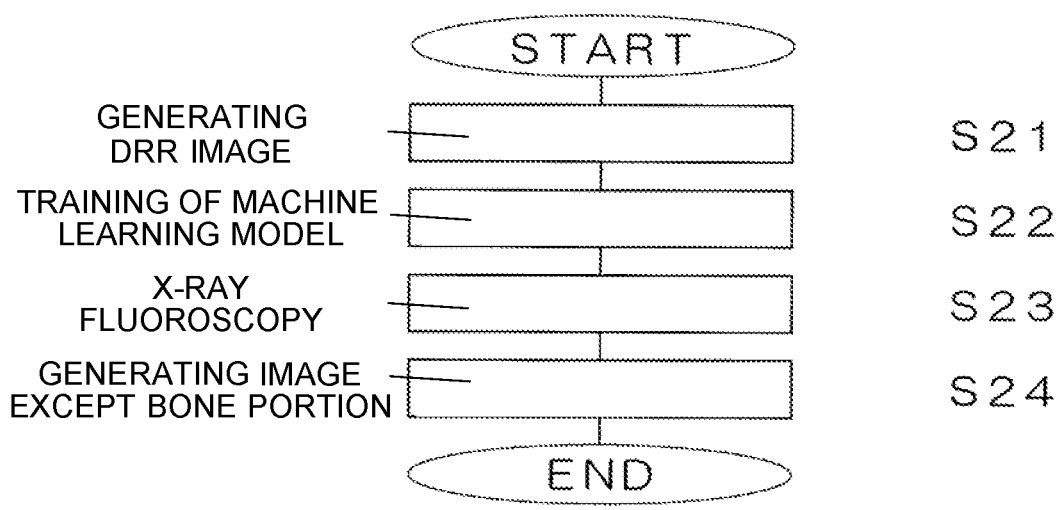
FIG. 12 is a flowchart showing an operation performed by the image generating device according to the modified example when generating an image which is an X-ray image of an area including the bone portions of a subject with the bone portions removed.

FIG. 12 is a flowchart showing an operation performed by the image generating device according to this modified example when generating an image which is an X-ray image of an area including the bone portions of a subject with the bone portions removed.

When the image generating operation is to be performed, the DRR imager 81 shown in FIG. 2 generates a first DRR image showing an area including bone portions and a second DRR image showing the regions except the bone portions in advance of the execution of X-ray fluoroscopy for a subject, by performing, for a set of four-dimensional CT image data obtained from the CT device 72, a virtual fluoroscopic projection simulating a geometric fluoroscopy condition of the X-ray irradiator 100 and X-ray detector 200 of the X-ray fluorography device shown in FIG. 1 (Step S21). When the second DRR image showing the regions except the bone portions is to be generated, all areas with the CT values equal to or less than a specific level are selected as the regions except the bone portions for the generation of the DRR image. For example, all areas with the CT value equal to or less than 200 HU may be recognized as the regions except the bone portions for the generation of the DRR image.

After the previously described processes have been completed, the training section 82 trains a machine learning model for recognizing the regions except the bone portions, by performing machine learning using the first DRR images as the input layer and the second DRR images as the output layer (Step S22). Once again, fully convolutional networks (FCNs) are used in this machine learning, for example.

After the machine learning model has been trained through the previously described processes, the X-ray fluoroscopy for the subject is initiated (Step S23).

Next, the image converter 83 performs conversion using the machine learning model (convolution layer) which has been trained, to generate an image of the regions except the bone portions (Step S24). Specifically, for the X-ray images obtained at a predetermined frame rate by the X-ray fluoroscopy, an X-ray image showing the regions except the bone portions (soft tissues) is generated as the output layer for each frame of the X-ray image, using the trained machine learning model.

As described to this point, in the image generating device according to this modified example, the convolution layer to be used as the machine learning model is trained by machine learning using the first DRR images as the input layer and the second DRR images as the output layer. Subsequently, an X-ray image as the input layer is converted by means of the trained machine learning model to obtain an X-ray image showing the regions except the bone portions as the output layer. Thus, an image showing the regions except the bone portions can be obtained in real time.

Figure 13:
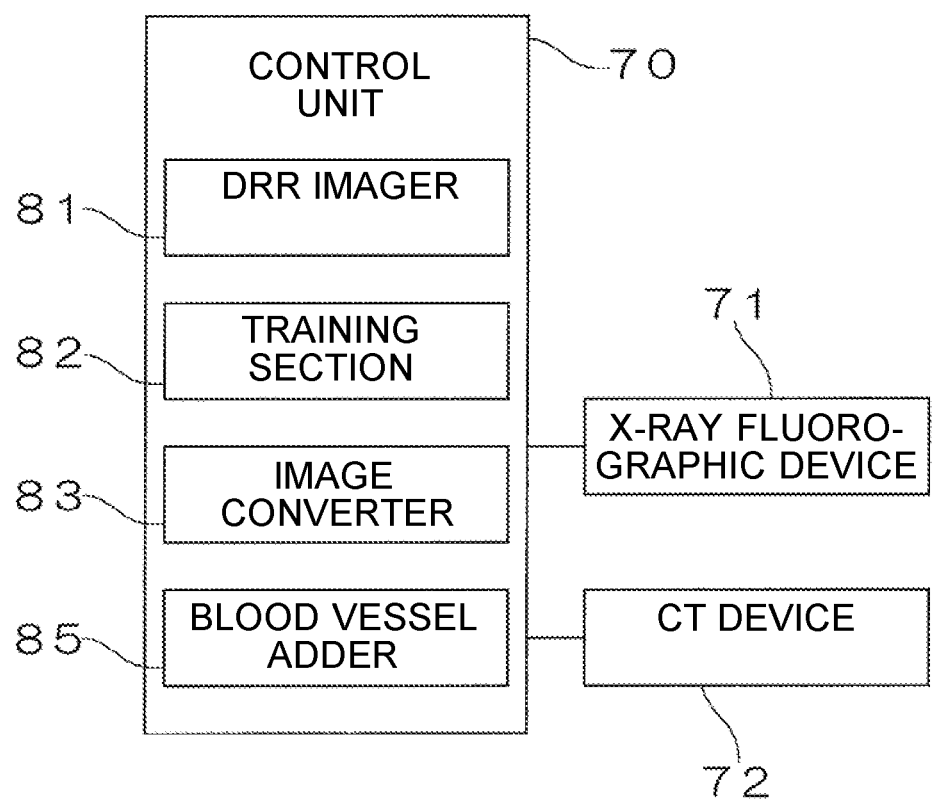
FIG. 13 is a block diagram showing the control system of an image generating device according to the second embodiment of the present invention.

Next, the configuration of an image generating device according to the second embodiment of the present invention is described. FIG. 13 is a block diagram showing the control system of an image generating device according to the second embodiment of the present invention.

The image generating device according to the second embodiment is configured to generate an image of a blood vessel of the subject with a contrast dye injected. As with the image generating device according to the first embodiment, the present device includes a control unit 70 configured to control the entire device. The control unit 70 is connected to the X-ray fluorography device 71 shown in FIG. 1. The control unit 70 is also connected online or offline to the CT device 72, which performs CT scan for a subject and stores the CT images.

As will be described later, the control unit 70 includes: a DRR imager 81 configured to generate a first DRR image of an area including a blood vessel and a second DRR image showing the blood vessel, by performing, for a set of CT image data of an area including the blood vessel of a subject, a virtual fluoroscopic projection simulating a geometric fluoroscopy condition of an X-ray irradiator 100 and an X-ray detector 200 for the subject; a training section 82 configured to generate a machine learning model for recognizing the blood vessel, by performing machine learning using the first DRR image and the second DRR image serving as a training image; an image converter 83 configured to perform conversion of the X-ray image of the area including the blood vessel of the subject, using the machine learning model trained in the training section 82, to generate an image showing the blood vessel; and a blood vessel adder 85 configured to add, to the X-ray image, an image showing the blood vessel with a contrast dye injected. The first DRR image is a DRR image obtained by removing the dye-injected blood vessel from a DRR image including the dye-injected blood vessel.

Figure 14:
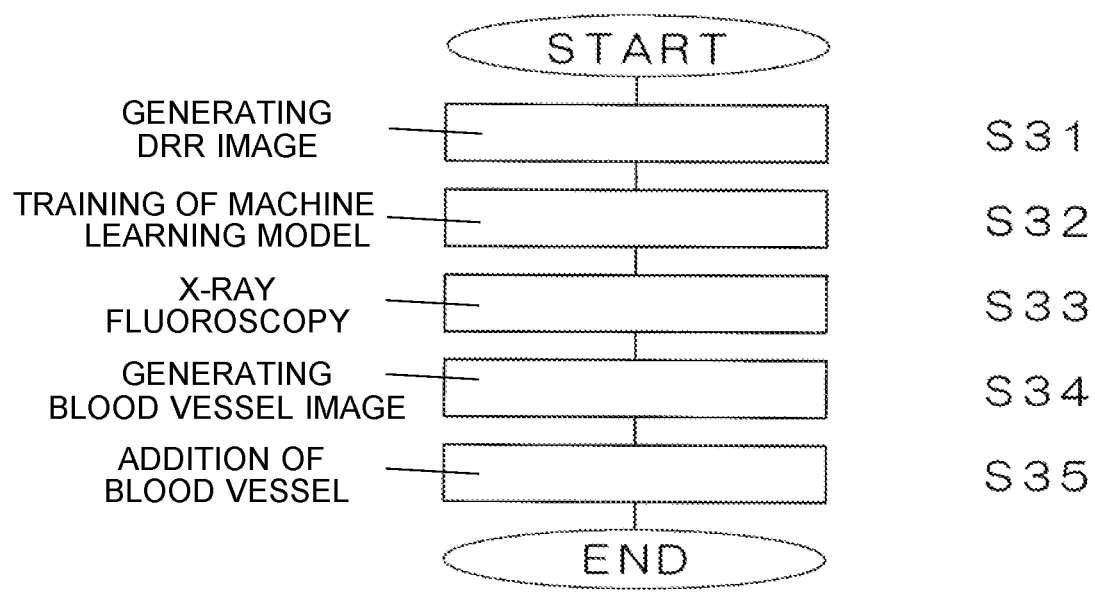
FIG. 14 is a flowchart showing an operation performed by the image generating device according to the second embodiment of the present invention when generating an image of blood vessels of a subject with a contrast dye injected.

The operation performed by the image generating device having the previously described configuration to detect the region of a blood vessel of a subject with a contrast dye injected and generate an image of the dye-injected blood vessel of the subject is hereinafter described. FIG. 14 is a flowchart showing an operation performed by the image generating device according to the second embodiment of the present invention when generating an image of a blood vessel of a subject with a contrast dye injected. The basic idea for identifying a blood vessel of a subject with a contrast dye injected is the same as that of the previously described processes of FIG. 3 in the first embodiment.

When the image generating operation is to be performed, the DRR imager 81 shown in FIG. 13 generates a first DRR image showing an area including a dye-injected blood vessel and a second DRR image showing the dye-injected blood vessel in advance of the execution of X-ray fluoroscopy for a subject, by performing, for a set of four-dimensional CT image data obtained from the CT device 72, a virtual fluoroscopic projection simulating a geometric fluoroscopy condition of the X-ray irradiator 100 and X-ray detector 200 of the X-ray fluorography device shown in FIG. 1 (Step S31). The CT images used in this step are CT images taken after the injection of the contrast dye into the blood vessel (contrast CT images). When generating the second DRR image showing the dye-injected blood vessel, an operator specifies an area whose CT value is within a predetermined range for the generation of the DRR image. For example, the operator may specify an area of a blood vessel, in which case an area which continuously extends with the CT value matching that of the specified area can be recognized as an area of the blood vessel. Anatomical information may also be used as a basis for recognizing the area of the blood vessel.

For the generation of the first and second DRR images, the virtual projection as shown in FIG. 5 is performed, as in the first embodiment. When a DRR image is to be generated, one or more parameters for the generation of the DRR image, including one or both of the coordinates and angle of projection for the CT image data 300, are varied to generate the DRR image, or alternatively, an image processing operation including at least one of the operations of translation, rotation, deformation and resizing by a small amount is performed, as in the first embodiment. The generated DRR image is further subjected to at least one of the operations of contrast change, noise addition and edge enhancement, as in the first embodiment.

Figure 15:
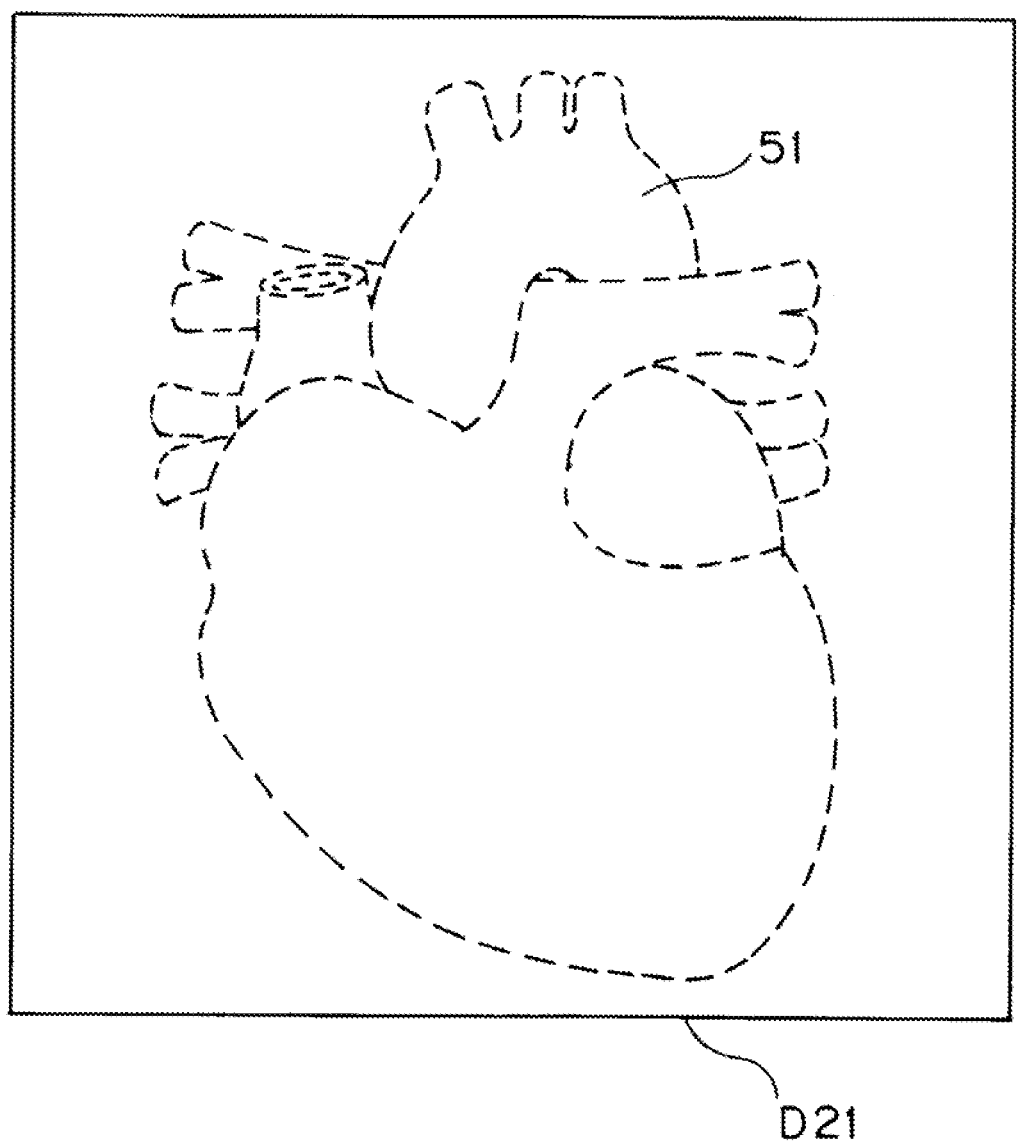
FIG. 15 is a rough sketch of the first DRR image D21 showing a heart 51.
Figure 16:
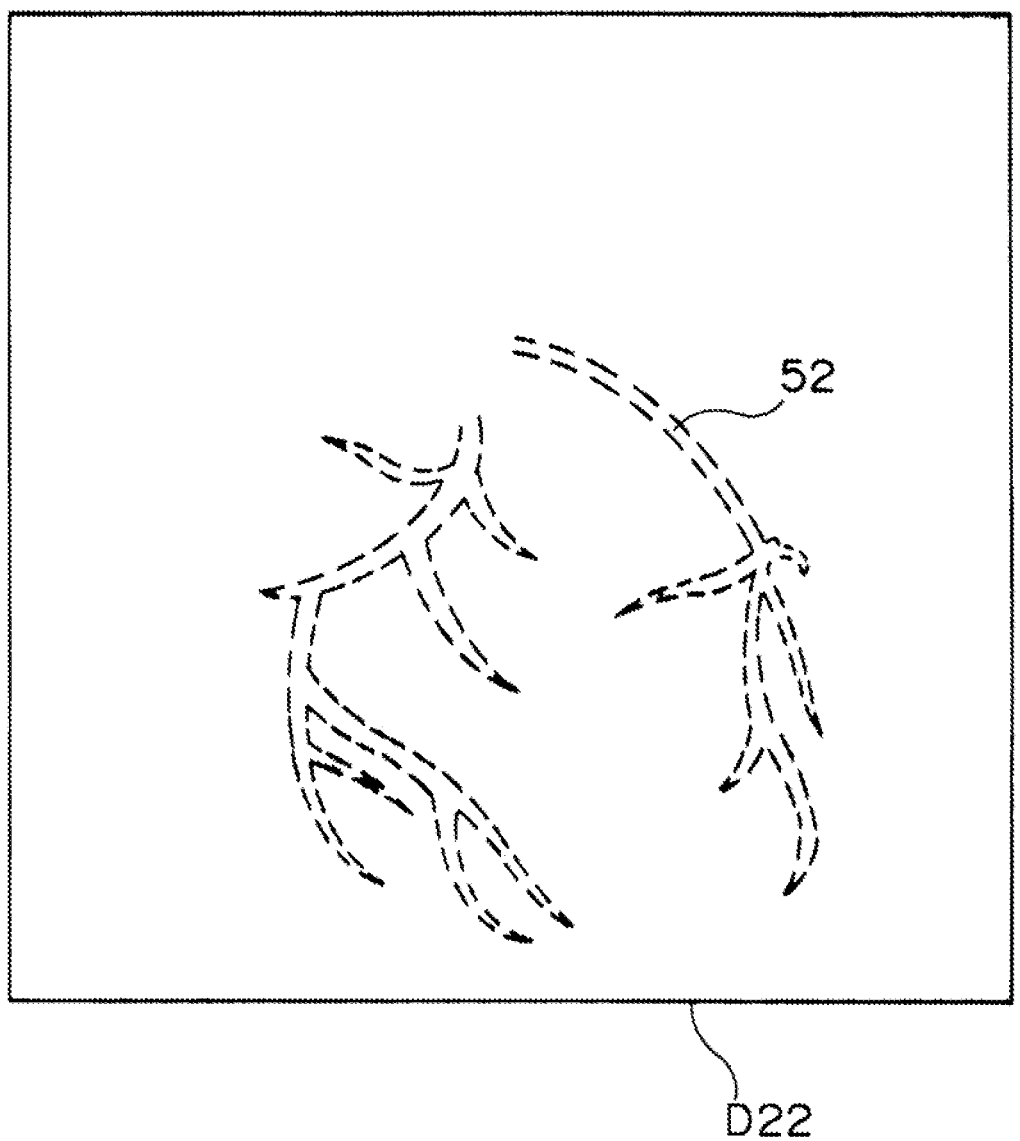
FIG. 16 is a rough sketch of the second DRR image D22 showing blood vessels 52 with a contrast dye injected.

FIG. 15 is a rough sketch of the first DRR image D21 showing a heart 51 generated in the previously described manner. FIG. 16 is a rough sketch of the second DRR image D22 showing blood vessels 52 with a contrast dye injected. The first DRR image D21 is an image obtained by removing the dye-injected blood vessels 52 from a DRR image showing the heart 51 and dye-injected blood vessels 52.

After the previously described processes have been completed, the training section 82 trains a machine learning model for recognizing the dye-injected blood vessels 52, by performing machine learning using the first DRR images D21 as the input layer and the second DRR images D22 as the output layer (Step S32). Once again, FCNs are used in this machine learning, for example. The convolutional neural networks used in the FCNs have a configuration as already shown in FIG. 3. That is to say, in the case of training the machine learning model, the input layer is the first DRR image D21, and the output layer is the second DRR image D22.

Figure 17:
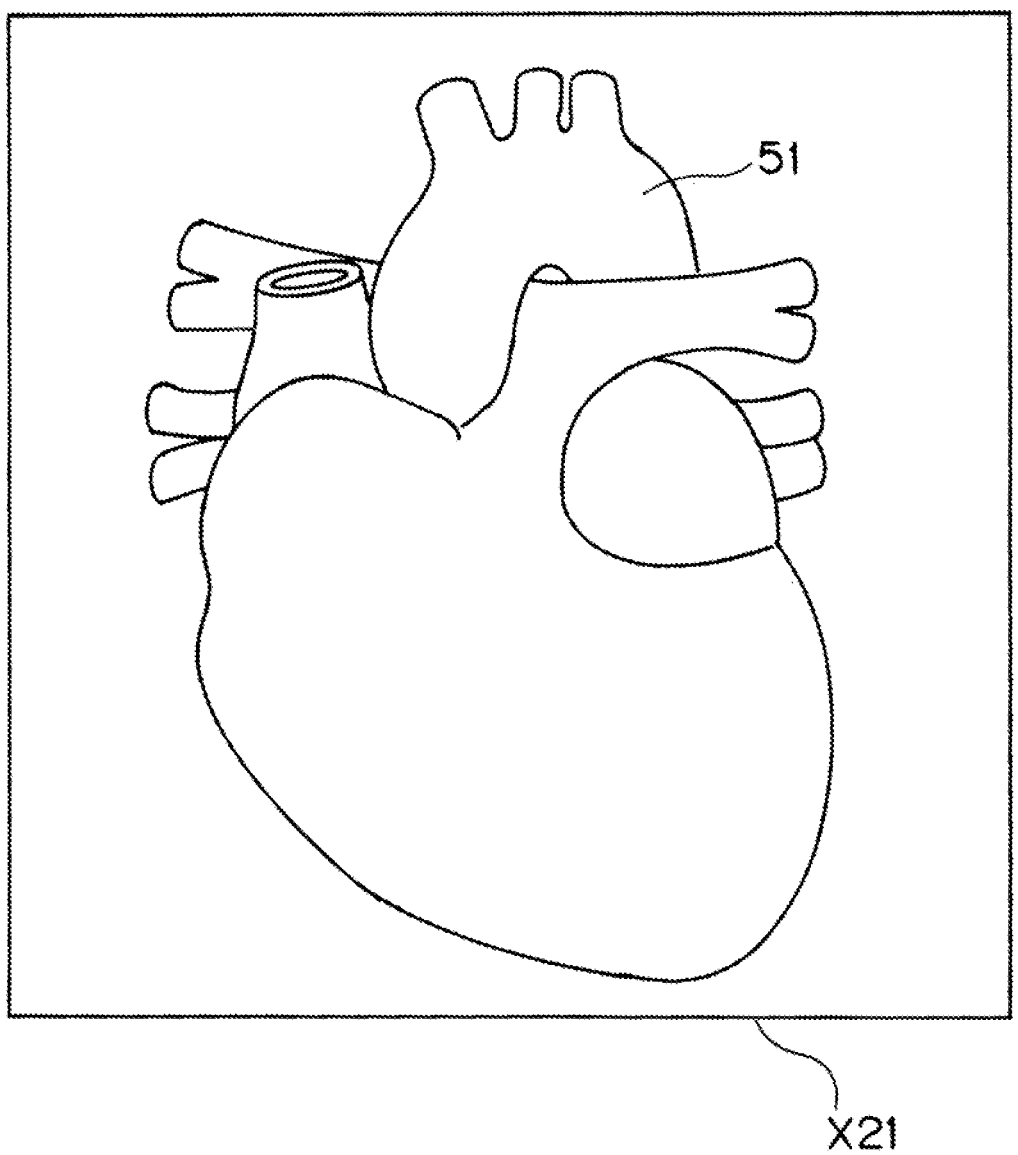
FIG. 17 is a rough sketch of an X-ray image X21 obtained by X-ray fluoroscopy.

After the machine learning model has been trained through the previously described processes, the X-ray fluoroscopy for the subject is initiated (Step S33). FIG. 17 is a rough sketch of an X-ray image X21 obtained by the X-ray fluoroscopy. The X-ray fluoroscopy is performed with no contrast dye injected in the subject. Therefore, the blood vessels are not clearly shown in the X-ray image X21.

Figure 18:
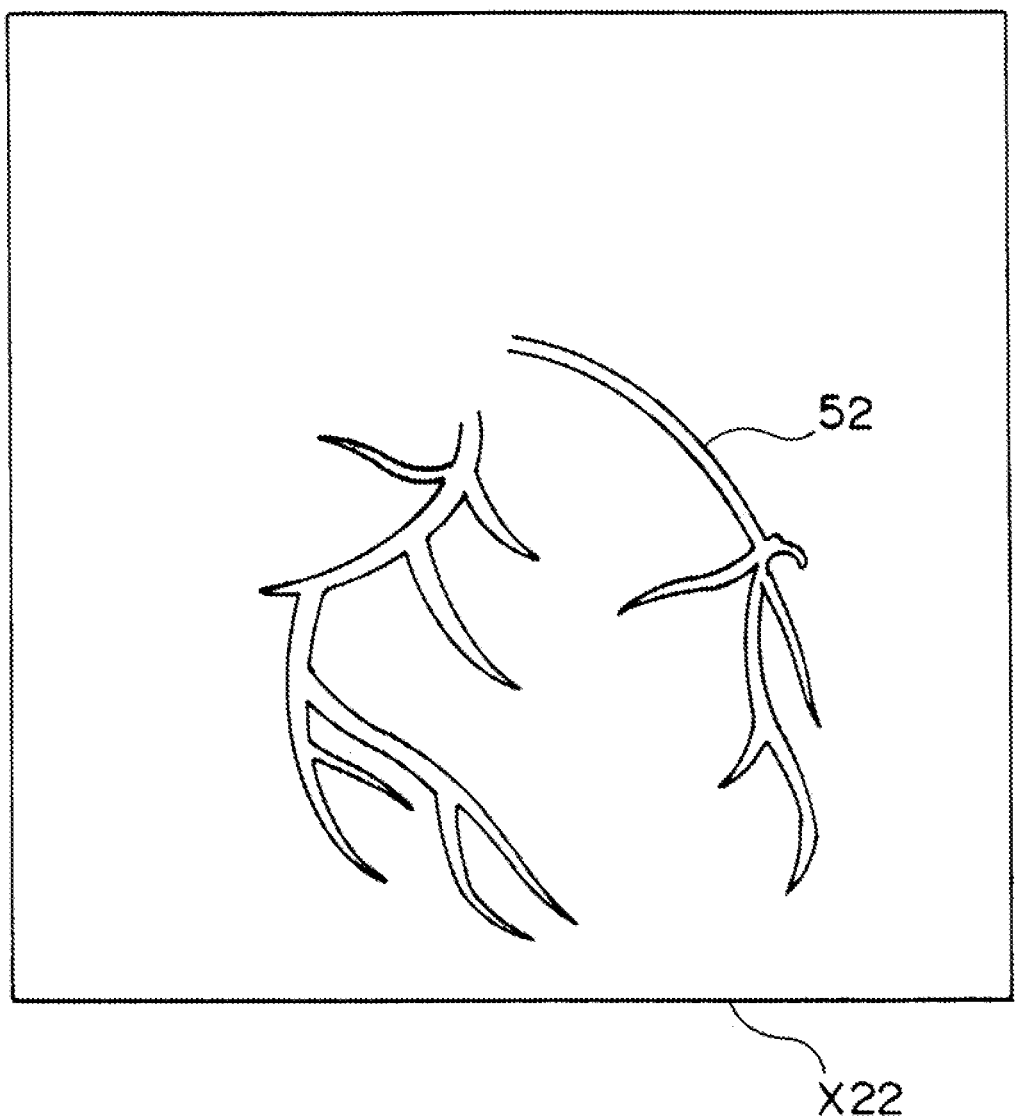
FIG. 18 is a rough sketch of an X-ray image X22 of the blood vessels 52 with a contrast dye injected, obtained by conversion.

Next, the image converter 83 performs conversion using the machine learning model (convolution layer) which has been trained, to generate an image of the dye-injected blood vessels 52 (Step S34). Specifically, for the X-ray images obtained at a predetermined frame rate by the X-ray fluoroscopy, an X-ray image showing the dye-injected blood vessels 52 is generated as the output layer for each frame of the X-ray image, using the trained machine learning model. FIG. 18 is a rough sketch of an X-ray image X22 of the dye-injected blood vessels 52 obtained by the conversion.

Subsequently, the blood vessel adder 85 adds, to the X-ray image X21 of the subject, the X-ray image X22 of the dye-injected blood vessels 52 obtained by the conversion (Step S35). Although the X-ray image X22 of the blood vessels 52 already allows the dye-injected blood vessels 52 to be clearly recognized, the X-ray image X22 of the dye-injected blood vessels 52 obtained by the conversion is further added to the X-ray image X21 of the subject so that the blood vessels 52 can be recognized along with the heart 51 and other related regions. A specific color may be given to the dye-injected blood vessels 52 in the adding process to highlight the dye-injected blood vessels 52.

In the previous description, images in which no dye-injected blood vessels 52 are present are used as the first DRR image D21 and X-ray image X21. Images in which both the heart 51 and the dye-injected blood vessels 52 are present may also be used as the first DRR image D21 and X-ray image X21.

Figure 19:
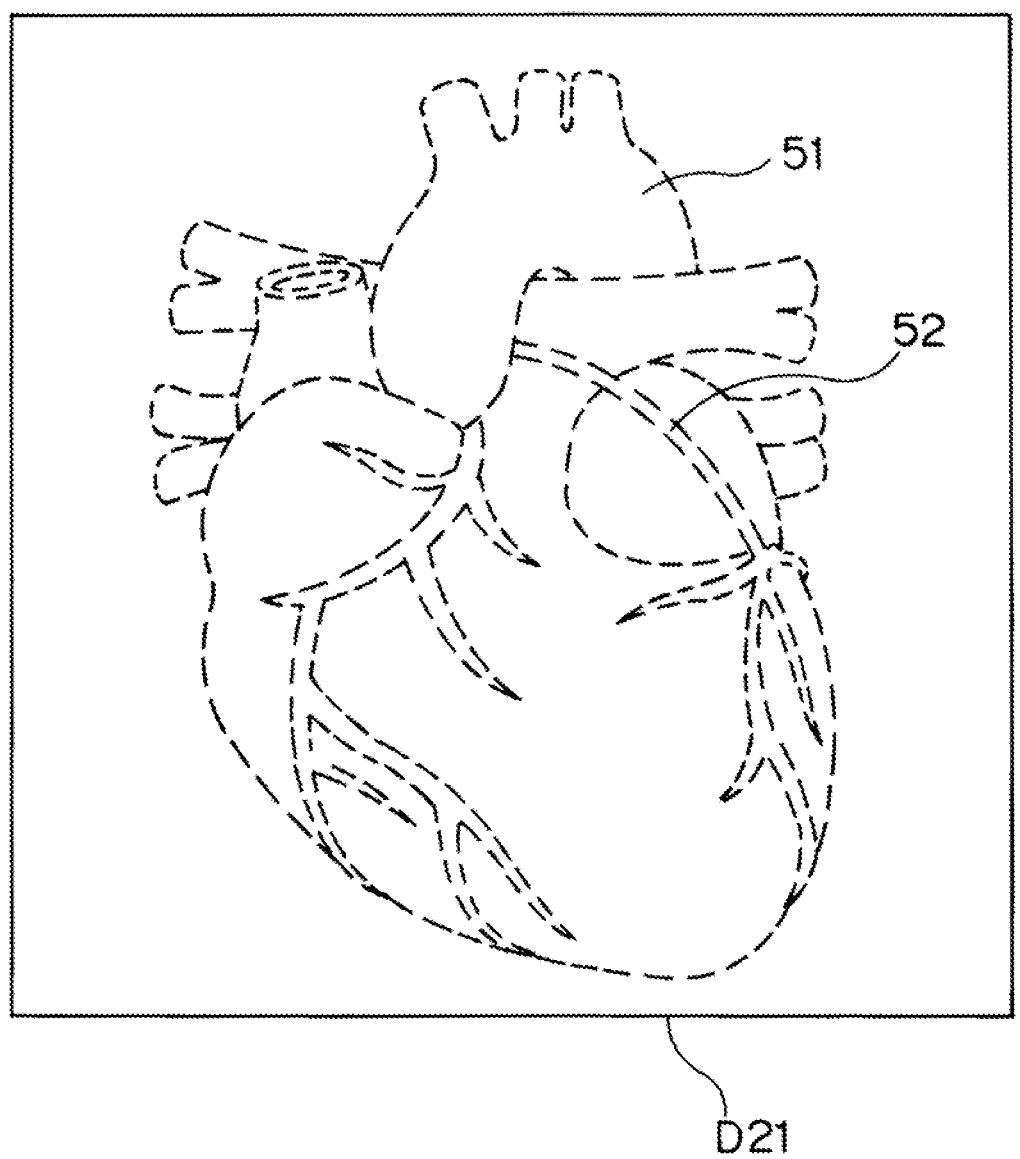
FIG. 19 is a rough sketch of the first DRR image D21.
Figure 20:
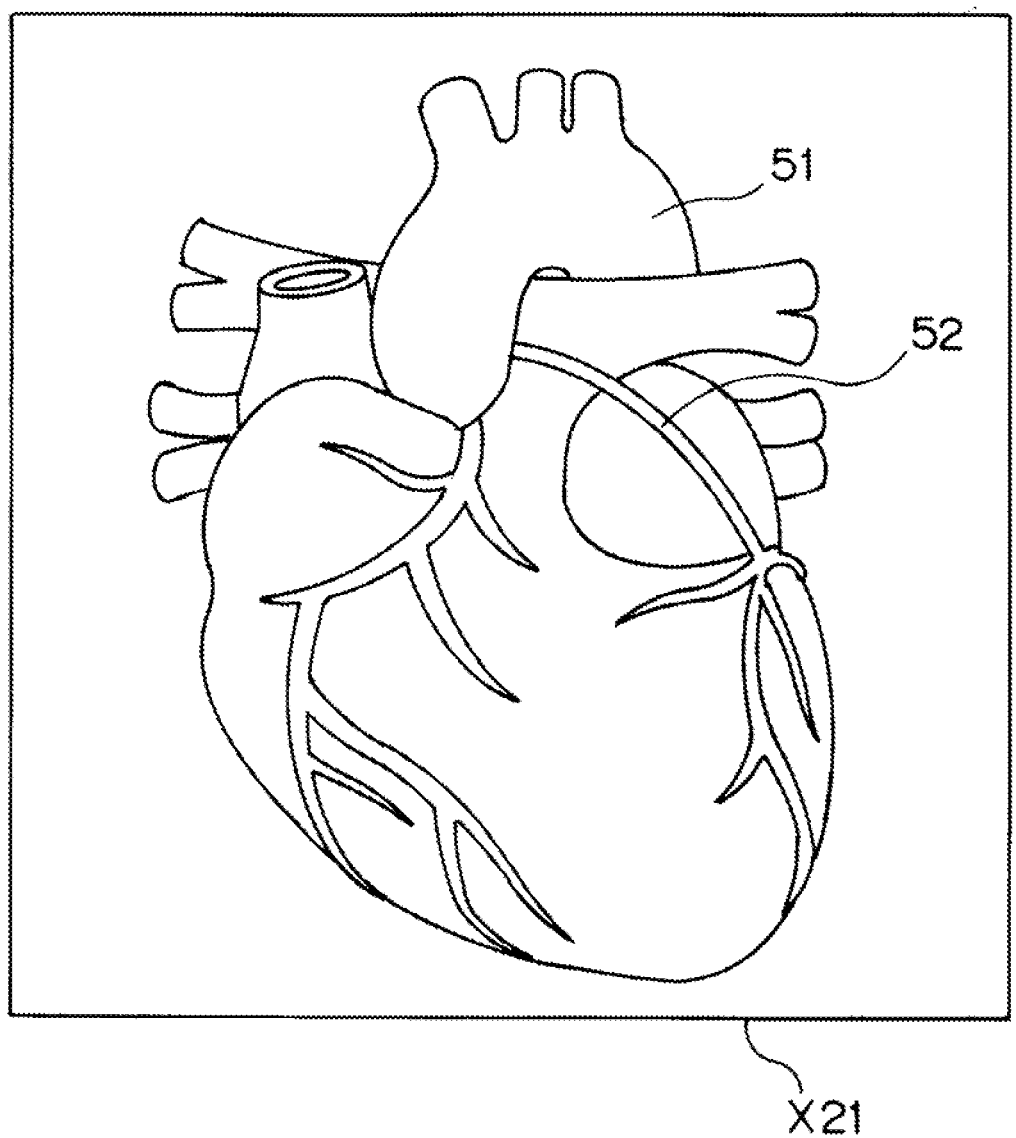
FIG. 20 is a rough sketch of the X-ray image X21 obtained by X-ray fluoroscopy.

In this case, the first DRR image shows both the heart 51 and the blood vessels 52. FIG. 19 is a rough sketch of the first DRR image D21 in the present case. The X-ray fluorography should be performed with the contrast dye injected in the body of the subject. FIG. 20 is a rough sketch of the X-ray image X21 obtained by X-ray fluoroscopy in the present case. A method similar to the previously described embodiment can also be used in the present case to obtain an X-ray image X22 of the dye-injected blood vessels 52 as shown in FIG. 18. The process of adding blood vessels shown in FIG. 14 (Step S35) is unnecessary in the case of omitting the removal of the image of the dye-injected blood vessels.

Figure 21:
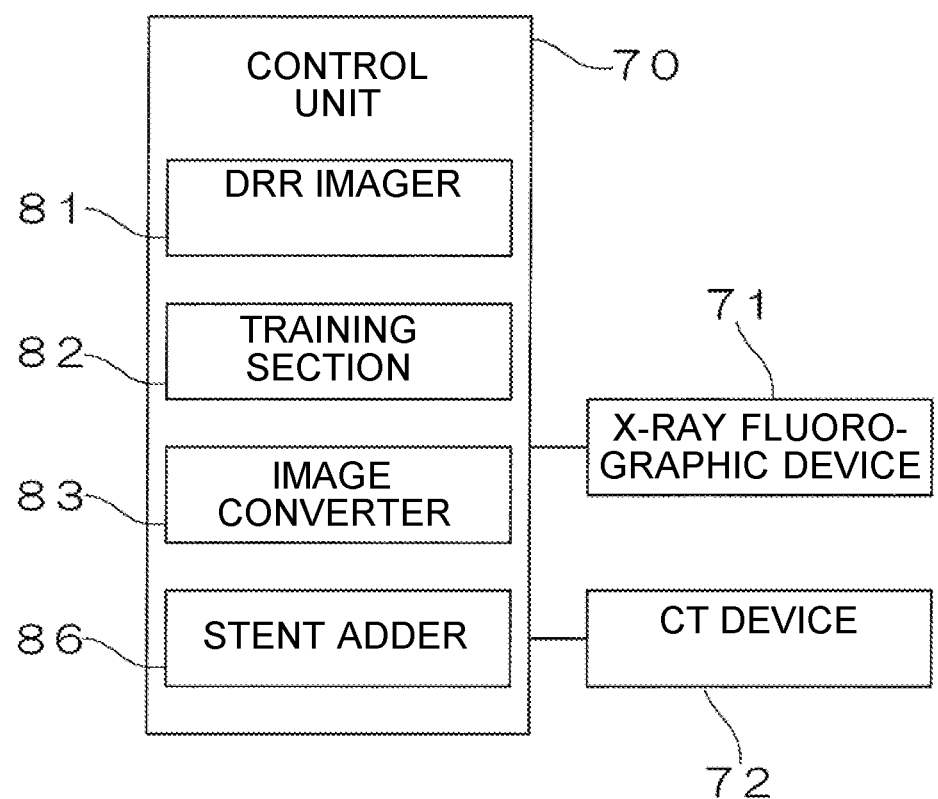
FIG. 21 is a block diagram showing the control system of an image generating device according to the third embodiment of the present invention.

Next, the configuration of an image generating device according to the third embodiment of the present invention is described. FIG. 21 is a block diagram showing the control system of an image generating device according to the third embodiment of the present invention.

The image generating device according to the third embodiment is configured to generate an image by adding a stent (e.g. a bioabsorbable stent) placed in the body of the subject to an X-ray image of a subject. As with the image generating devices according to the first and second embodiments, the present device includes a control unit 70 configured to control the entire device. The control unit 70 is connected to the X-ray fluorography device 71 shown in FIG. 1. The control unit 70 is also connected online or offline to the CT device 72, which performs CT scan for a subject and stores the CT images.

As will be described later, the control unit 70 includes: a DRR imager 81 configured to generate a first DRR image showing an area including a stent and a second DRR image showing the stent, by performing, for a set of CT image data of an area including a stent placed in the body of a subject, a virtual fluoroscopic projection simulating a geometric fluoroscopy condition of an X-ray irradiator 100 and an X-ray detector 200 for the subject; a training section 82 configured to generate a machine learning model for recognizing the stent, by performing machine learning using the first DRR image and the second DRR image serving as a training image; an image converter 83 configured to perform conversion of the X-ray image of the area including the stent placed in the body of the subject, using the machine learning model trained in the training section 82, to generate an image showing the stent; and a stent adder 86 configured to add the X-ray image showing the stent placed in the body of the subject to the X-ray image.

Figure 22:
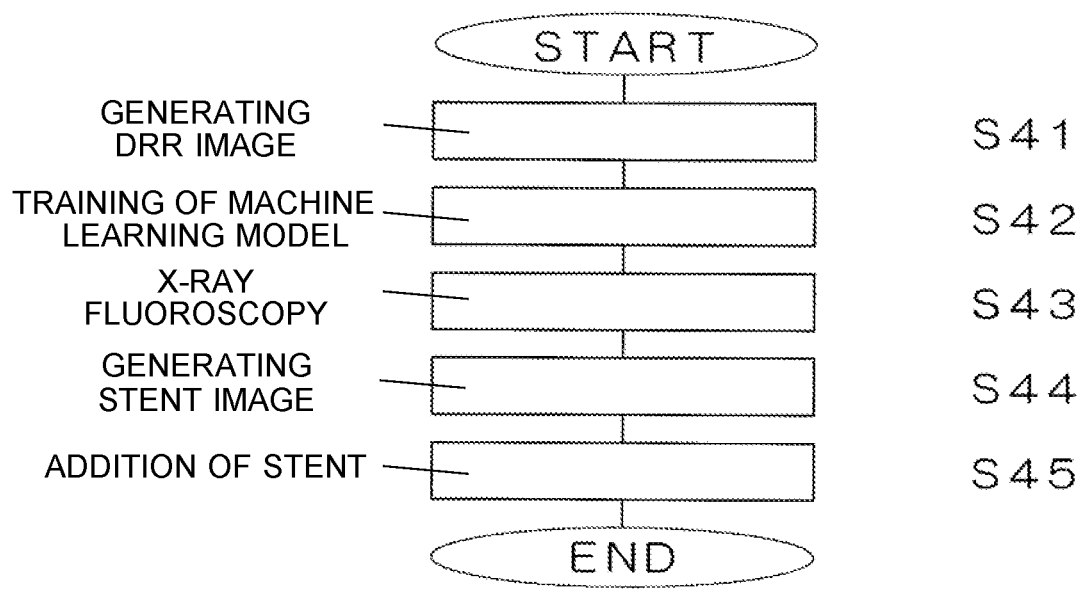
FIG. 22 is a flowchart showing an operation performed by the image generating device according to the third embodiment of the present invention when generating an image of a stent placed in the body of a subject.

The operation performed by the image generating device having the previously described configuration to detect the region of a stent placed in the body of a subject and generate an image of the stent placed in the body of the subject is hereinafter described. FIG. 22 is a flowchart showing an operation performed by the image generating device according to the third embodiment of the present invention when generating an image of a stent placed in the body of a subject. The basic idea for identifying a stent placed in the body of a subject is the same as that of the previously described processes of FIG. 3 in the first embodiment.

When the image generating operation is to be performed, the DRR imager 81 shown in FIG. 21 generates a first DRR image showing an area including a stent placed in the body of a subject and a second DRR image showing the stent placed in the body of the subject in advance of the execution of X-ray fluoroscopy for a subject, by performing, for a set of four-dimensional CT image data obtained from the CT device 72, a virtual fluoroscopic projection simulating a geometric fluoroscopy condition of the X-ray irradiator 100 and X-ray detector 200 of the X-ray fluorography device shown in FIG. 1 (Step S41). When generating the second DRR image showing the stent placed in the body of the subject, an operator specifies an area whose CT value is within a predetermined range for the generation of the DRR image. As in the case of using a bioabsorbable stent, if it is difficult to recognize the region of the stent on the CT image, the operator can manually superpose a separate image of the stent on the CT image to generate the second DRR image showing the stent.

For the generation of the first and second DRR images, the virtual projection as shown in FIG. 5 is performed, as in the first embodiment. When a DRR image is to be generated, one or more parameters for the generation of the DRR image, including one or both of the coordinates and angle of projection for the CT image data 300, are varied to generate the DRR image, or alternatively, an image processing operation including at least one of the operations of translation, rotation, deformation and resizing by a small amount is performed, as in the first embodiment. The generated DRR image is further subjected to at least one of the operations of contrast change, noise addition and edge enhancement, as in the first embodiment.

Figure 23:
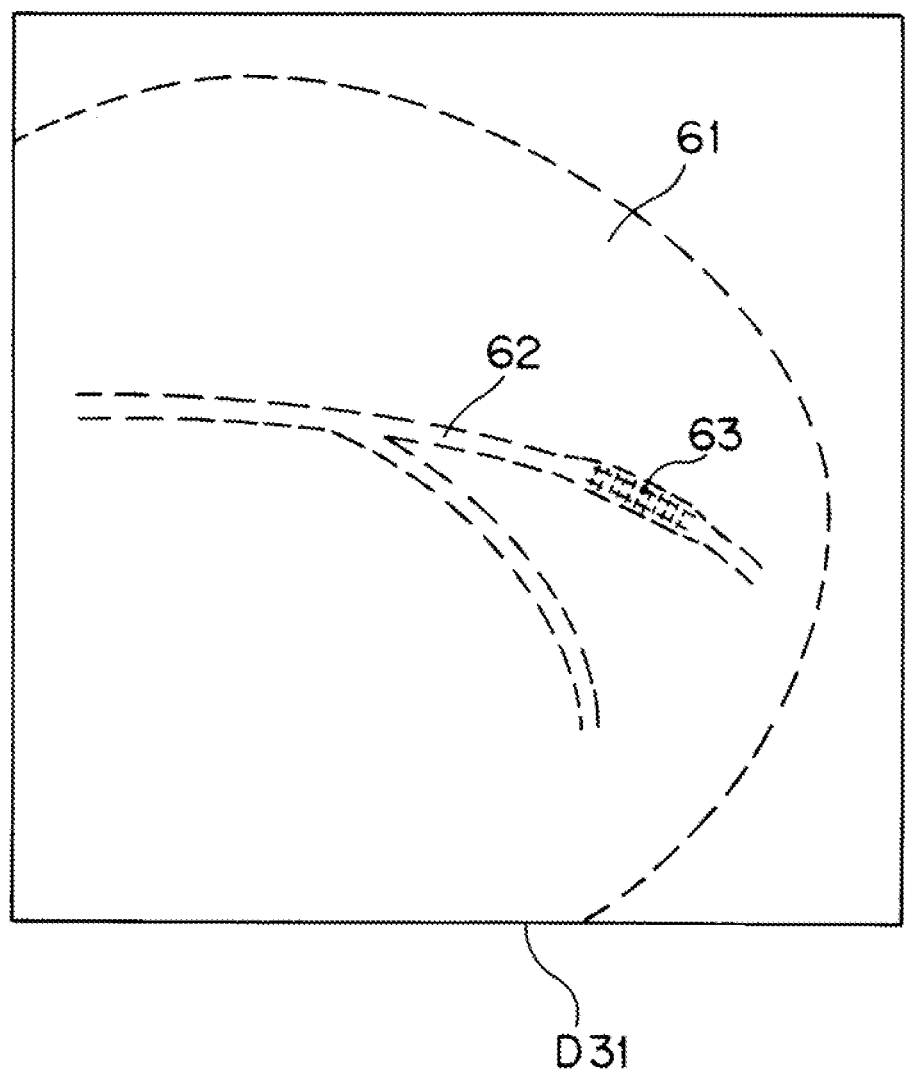
FIG. 23 is a rough sketch of the first DRR image D31 showing a heart 61, blood vessel 62 and stent 63.
Figure 24:
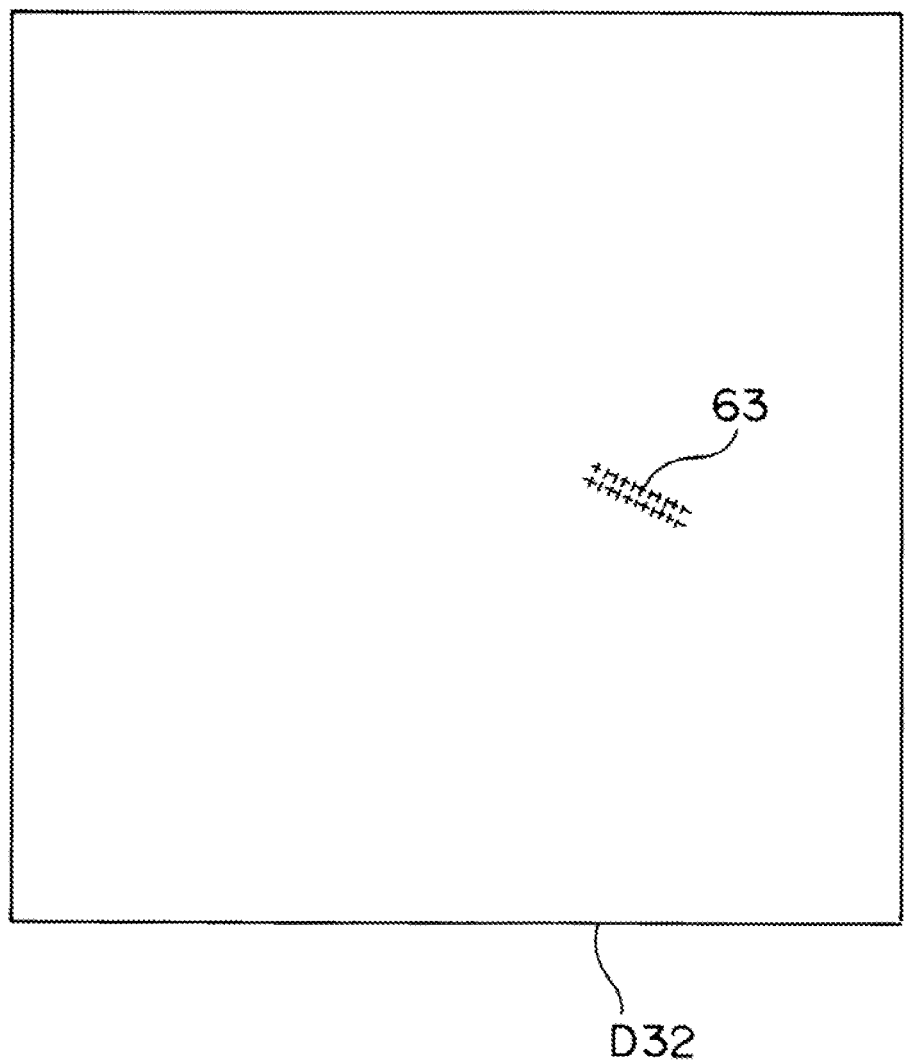
FIG. 24 is a rough sketch of the second DRR image D32 showing the stent 63.

FIG. 23 is a rough sketch of the first DRR image D31 showing the heart 61, blood vessel 62 and stent 63. FIG. 24 is a rough sketch of the second DRR image D32 showing the stent 63. As noted earlier, the stent 63 may not be recognizable in the first DRR image D31.

After the previously described processes have been completed, the training section 82 trains a machine learning model for recognizing the stent 63 placed in the body of the subject, by performing machine learning using the first DRR images D31 as the input layer and the second DRR images D32 as the output layer (Step S42). Once again, FCNs are used in this machine learning, for example. The convolutional neural networks used in the FCNs have a configuration as already shown in FIG. 3. That is to say, in the case of training the machine learning model, the input layer is the first DRR image D31, and the output layer is the second DRR image D32.

Figure 25:
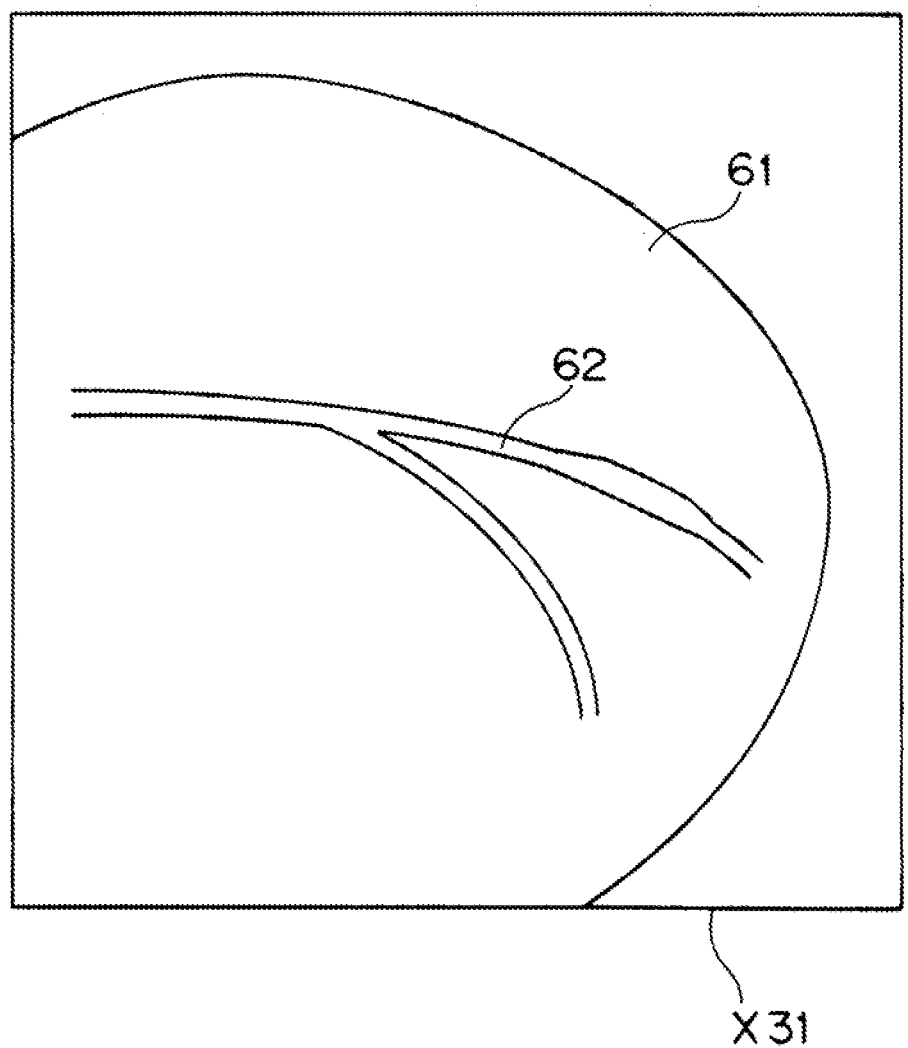
FIG. 25 is a rough sketch of an X-ray image X31 obtained by X-ray fluoroscopy.

After the machine learning model has been trained through the previously described processes, the X-ray fluoroscopy for the subject is initiated (Step S43). FIG. 25 is a rough sketch of an X-ray image X31 obtained by the X-ray fluoroscopy. The stent 63 is not displayed in this X-ray image X31.

Figure 26:
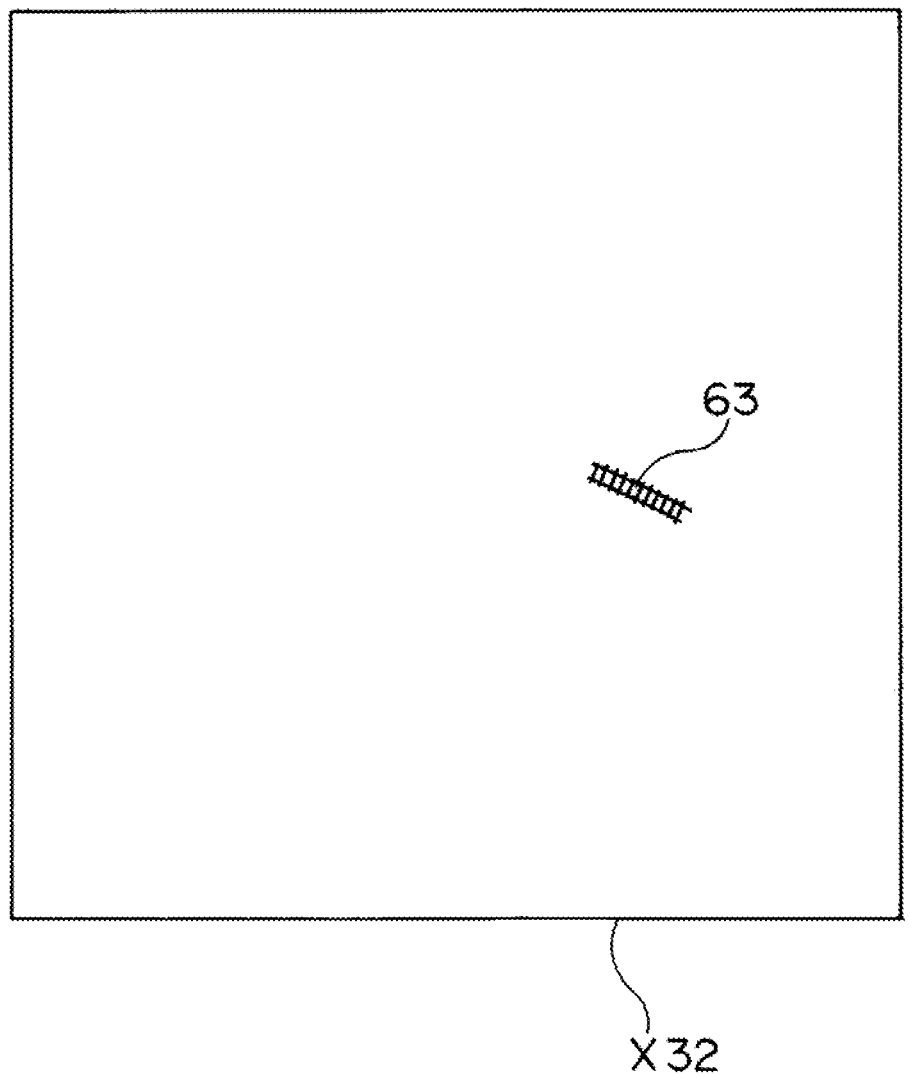
FIG. 26 is a rough sketch of an X-ray image X32 of the stent 63 placed in the body of a subject.

Next, the image converter 83 performs conversion using the machine learning model (convolution layer) which has been trained, to generate an image of the stent 63 placed in the body of the subject (Step S44). Specifically, for the X-ray fluoroscopic images obtained at a predetermined frame rate by the X-ray fluoroscopy, an X-ray image showing the stent 63 placed in the body of the subject is generated as the output layer for each frame of the X-ray image, using the trained machine learning model. FIG. 26 is a rough sketch of an X-ray image X32 of the stent 63 placed in the body of the subject, obtained by the conversion.

Figure 27:
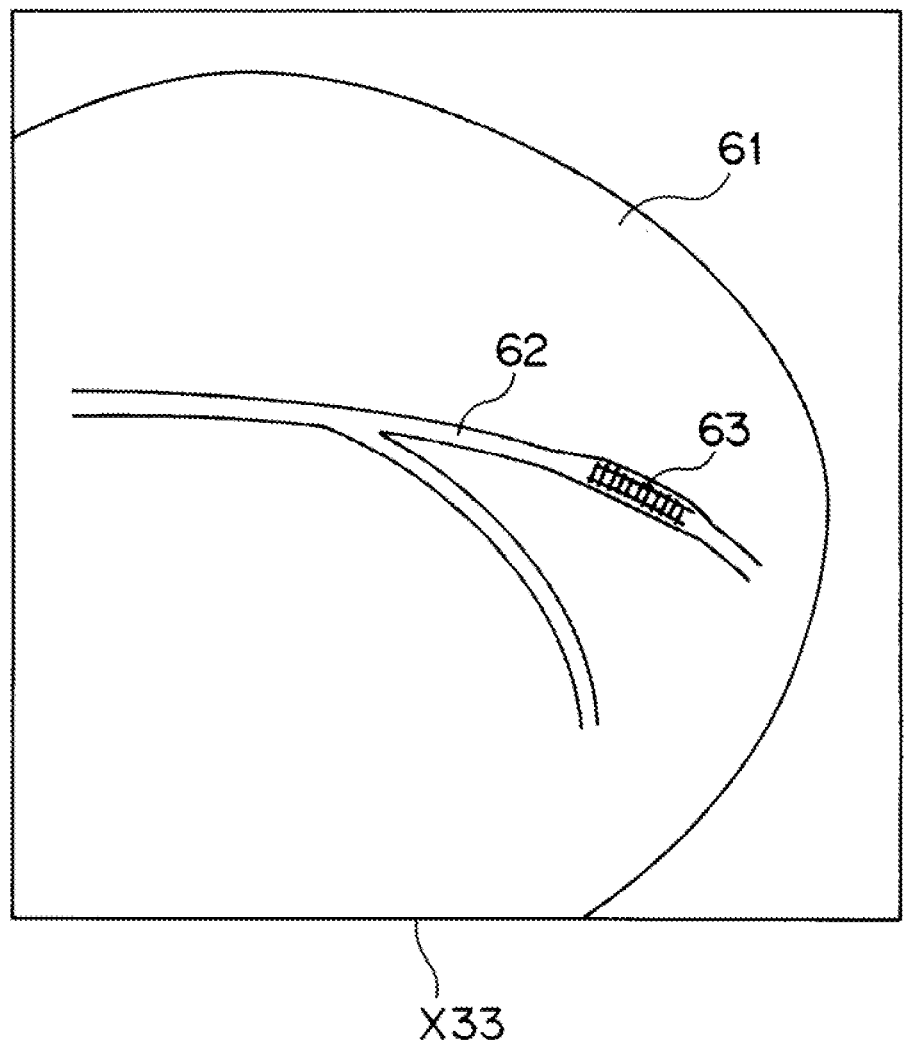
FIG. 27 is a rough sketch of an X-ray image X33 showing the heart 61, blood vessel 62 and stent 63.

Subsequently, the stent adder 85 adds, to the X-ray image X31 of the subject, the X-ray image X32 of the stent 63 placed in the body of the subject, obtained by the conversion (Step S45). FIG. 27 is a rough sketch of an X-ray image X32 of the heart 61, blood vessel 62 and stent 63.

Thus, the X-ray image X33 in which the stent 63 is superposed on the X-ray image X31 showing the heart 61 and blood vessel 62 of the subject is obtained. Even when a bioabsorbable stent or similar type of stent that cannot be recognized by X-ray spectroscopy is used as the stent 63, the location of the stent 63 can be identified from feature quantities around the stent 63, and the stent 63 can be recognized on the X-ray image X33 along with the heart 61, blood vessel 62 and other related portions of the subject.

REFERENCE SIGNS LIST

11 Device Body
13 C-Arm
15 Monitor Unit
16 Input Section
17 Display Section
21 X-Ray Tube
23 Collimator
41 Bone Portion
42 Soft Tissue
51 Heart
52 Blood Vessel
61 Heart
62 Blood Vessel
63 Stent
70 Control Unit
71 X-Ray Fluorography Device
72 Computed Tomography (CT) Device
81 DRR imager
82 Training Section
83 Image converter
84 Bone Portion Subtractor
85 Blood Vessel Adder
86 Stent Adder

The invention claimed is:

1. An image generating device, comprising:
   a DRR imager configured to generate a first DRR image showing a first region and a second region of a subject and a second DRR image showing the first region, by performing, for a set of CT image data of the area including the first region of the subject, a virtual fluoroscopic projection simulating a geometric fluoroscopy condition of an X-ray irradiator and an X-ray detector for the subject; and
   an image converter configured to perform conversion of an X-ray image showing the first region and the second region of the subject into an image showing the first region, using a machine learning model that has undergone machine learning using the first DRR image for an input image and the second DRR image for a training image.

2. The image generating device according to claim 1, wherein:
   the first region is a bone portion; and
   the image generating device further comprises a bone portion subtractor configured to subtract an image showing the bone portion from the X-ray image.

3. The image generating device according to claim 1, wherein:

the first region is all regions except the bone portion of the subject.

4. The image generating device according to claim 1, wherein:
the first region is a blood vessel with a contrast dye injected.

5. The image generating device according to claim 4, wherein:
the first DRR image is a DRR image obtained by removing the dye-injected blood vessel from a DRR image including the dye-injected blood vessel, while the X-ray image is an X-ray image with no contrast dye injected; and
the image generating device further comprises a blood vessel adder configured to add an image showing the dye-injected blood vessel to the X-ray image.

6. The image generating device according to claim 1, wherein:
the first region is a stent placed in a body of the subject; and
the image generating device further comprises a stent adder configured to add an image showing the stent to the X-ray image.

7. A method for generating a machine learning model, comprising:
generating a first DRR image showing a first region and a second region of a subject and a second DRR image showing the first region, by performing, for a set of CT image data of the area including the first region of the subject, a virtual fluoroscopic projection simulating a geometric fluoroscopy condition of an X-ray irradiator and an X-ray detector for the subject; and
generating a machine learning model for performing conversion of an X-ray image showing the first region and the second region of the subject into an image showing the first region, by performing machine learning using the first DRR image for an input image and the second DRR image for a training image.

* * * * *